(12) United States Patent
Liu et al.

(10) Patent No.: US 11,267,777 B2
(45) Date of Patent: Mar. 8, 2022

(54) DEUTERATED EPI-743

(71) Applicant: Concert Pharmaceuticals, Inc., Lexington, MA (US)

(72) Inventors: Julie F. Liu, Lexington, MA (US); Darren H. Wong, Charleston, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 722 days.

(21) Appl. No.: 15/777,565

(22) PCT Filed: Nov. 18, 2016

(86) PCT No.: PCT/US2016/062760
§ 371 (c)(1),
(2) Date: May 18, 2018

(87) PCT Pub. No.: WO2017/087795
PCT Pub. Date: May 26, 2017

(65) Prior Publication Data
US 2021/0269382 A1 Sep. 2, 2021

Related U.S. Application Data

(60) Provisional application No. 62/257,567, filed on Nov. 19, 2015.

(51) Int. Cl.
*C07C 50/06* (2006.01)
*C07B 59/00* (2006.01)

(52) U.S. Cl.
CPC ............ *C07C 50/06* (2013.01); *C07B 59/001* (2013.01); *C07B 2200/05* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2011/0172312 A1 | 7/2011 | Miller et al. | |
| 2015/0119407 A1 | 4/2015 | Tung et al. | |

FOREIGN PATENT DOCUMENTS

| | | |
|---|---|---|
| WO | WO 1995/26325 | 10/1995 |
| WO | WO 2007/118651 | 10/2007 |
| WO | WO 2014/039862 | 3/2014 |

OTHER PUBLICATIONS

Baillie, "The Use of Stable Isotopes in Pharmacological Research," Pharmacology Rev, 1981, 33(2):81-132.
Blake et al., "Studies with Deuterated Drugs," J Pharm Sci, 1975, 64:367-391.
Browne, "Stable Isotope Techniques in Early Drug Development: An Economic Evaluation," J. Clin. Pharmacology, 1998, 38: 213-20.
Cherrah et al., "Study of Deuterium Isotope Effects on Protein Binding by Gas Chromatography/Mass Spectrometry. Caffeine and Deuterated Isotopomers," Biomed. and Environmental Mass Spectrometry, 1987, 14: 653-57.
Dyck et al., "Effects of Deuterium Substitution on the Catabolism of β-Phenylethylamine: An In Vivo Study," J. Neurochemistry, 1986, 46: 399-404.
Fisher et al., "The complexities inherent in attempts to decrease drug clearance by blocking sites of CYP-mediated metabolism," Curr. Opin. Drug Discov. Dev., 2006, 9(1):101-109.
Foster, "Deuterium isotope effects in studies of drug metabolism," Trends in Pharmaceutical Sciences, 1984, 524-527.
Foster, "Deuterium Isotope Effects in the Metabolism of Drugs and Xenobiotics: Implications for Drug Design," Adv. Drug Res., 1985, 14: 2-40.
Fukuto et al., "Determination of the Mechanism of Demethylenation of (Methylenedioxy)phenyl Compounds by Cytochrome P450 Using Deuterium Isotope Effects," J. Med. Chem. 1991, 34, 2871-76.
Gouyette, "Synthesis of Deuterium-labelled Elliptinium and its Use in Metabolic Studies," Biomed. and Environmental Mass Spectrometry, 1988, 15: 243-47.
Haskins, "The Application of Stable Isotopes in Biomedical Research," Biomed. Spectrometry, 1982, 9(7):269-77.
Honma et al., "The Metabolism of Roxatidine Acetate Hydrochloride," Drug Metab. Dispos, 1987, 15(4): 551-559.
International Search Report and Written Opinion in International Appln. No. PCT/US16/62760, dated Feb. 3, 2017, 11 pages.
Kushner et al. "Pharmacological uses and perspectives of heavy water and deuterated compounds," Can. J. Physiol. Pharmacol. 1999, 77: 79-88.

(Continued)

*Primary Examiner* — Joseph R Kosack
(74) *Attorney, Agent, or Firm* — Fish & Richardson P.C.

(57) ABSTRACT

This invention relates to novel α-tocotrienol quinones of Formula I: (I), and pharmaceutically acceptable salts thereof. This invention also provides compositions comprising a compound of this invention and the use of such compositions in methods of treating diseases and conditions that are beneficially treated by administering Vitamin E.

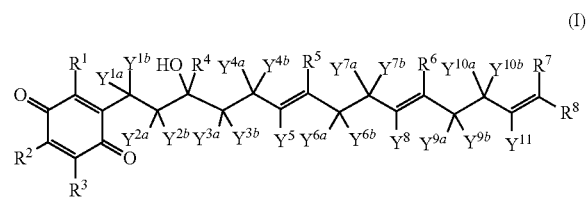

(I)

21 Claims, No Drawings

(56) References Cited

OTHER PUBLICATIONS

Pieniaszek et al., "Moricizine bioavailability via simultaneous, dual, stable isotope administrations: bioequivalence," J. Clin. Pharmacology, 1999, 39:817-25.

Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," Biol. Mass Spectrometry, 1993, 22:633-642.

Wolen, "The Application of Stable Isotopes to Studies of Drug Bioavailability and Bioequivalence," J. Clin. Pharmacology, 1986, 26:419-424.

DEUTERATED EPI-743

CLAIM OF PRIORITY

This application is a National Stage application under 35 U.S.C. § 371 of International Application No. PCT/US2016/062760, having an International Filing Date of Nov. 18, 2016, which claims the benefit of U.S. Provisional Application No. 62/257,567, filed Nov. 19, 2015. The entire contents of the foregoing are hereby incorporated by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to deuterated forms of α-tocotrienol quinones, and pharmaceutically acceptable salts thereof. In certain aspects, the present invention provides a compound of Formula I:

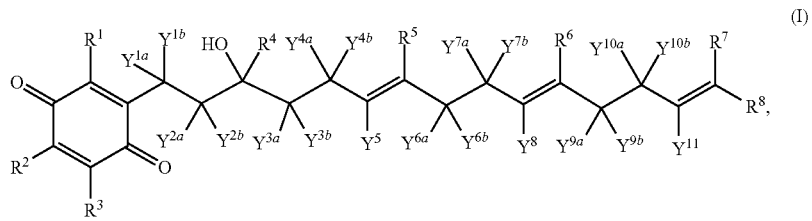

(I)

or a pharmaceutically acceptable salt thereof, wherein:
each of $R^1$, $R^2$, $R^3$, $R^4$, $R^5$, $R^6$, $R^7$ and $R^8$ is independently selected from —$CH_3$, —$CH_2D$, —$CHD_2$ and —$CD_3$;
each of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is independently selected from hydrogen and deuterium; and
when each of $R^1$, $R^2$, $R^3$, $R^4$, $R^5$, $R^6$, $R^7$ and $R^8$ is —$CH_3$, then at least one of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is deuterium.

Certain aspects of the present invention also provide compositions comprising a compound of this invention, including pharmaceutical compositions comprising a compound of this invention and a pharmaceutically acceptable carrier. Certain aspects of the present invention also provide the use of such compositions in methods of treating diseases and conditions that are beneficially treated by administering Vitamin E. Some exemplary embodiments include a method of treating a disease or condition selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, multisystem genetic disorders, Tourette's disease, metabolic disorders, mitochondrial disorders, Leber's hereditary optic neuropathy, and Huntington's disease, the method comprising the step of administering to a subject in need thereof a pharmaceutically acceptable composition of the present invention.

DETAILED DESCRIPTION OF THE INVENTION

EPI-743 also known as vatiquinone, ATQ3 and 2-((R,6E,10E)-3-hydroxy-3,7,11,15-tetramethylhexadeca-6,10,14-trien-1-yl)-3,5,6-trimethylcyclohexa-2,5-diene-1,4-dione, is a potent cellular protectant against oxidative stress and aging (Shrader, et al. Bioorg Med Chem Lett 21 (2011) 3693-3698). EPI-743 is a naturally occurring metabolite of α-tocotrienol.

EPI-743 is currently in numerous human clinical trials for indications including Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, Multisystem genetic disorders, Tourette's disease and non-specific metabolic and mitochondrial disorders. Positive clinical results for EPI-743 have been reported in Leber's hereditary optic neuropathy. The compound is also in preclinical development for Huntington's disease.

EPI-743 has been assigned orphan drug designation for the treatment of inherited mitochondrial respiratory chain diseases, Leigh's syndrome, Friedrich's disease and Rett's syndrome.

Despite the beneficial activities of EPI-743, there is a continuing need for new compounds to treat the aforementioned diseases and conditions.

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

As used herein, the term "subject" includes humans and non-human mammals. Non-limiting examples of non-human mammals include mice, rats, guinea pigs, rabbits, dogs, cats, monkeys, apes, pigs, cows, sheep, horses, etc.

It will be recognized that some variation of natural isotopic abundance occurs in a synthesized compound depending upon the origin of chemical materials used in the synthesis. Thus, a preparation of EPI-743 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts of the compounds of the invention.

A salt of a compound of this invention is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. In one embodiment, the acids commonly employed to form pharmaceutically acceptable salts include the above-listed inorganic and organic acids, wherein at least one hydrogen is replaced with deuterium.

The compounds of the present invention (e.g., compounds of Formula I or Ia) contain an asymmetric carbon atom. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

Certain aspects of the present invention provide a compound of Formula I:

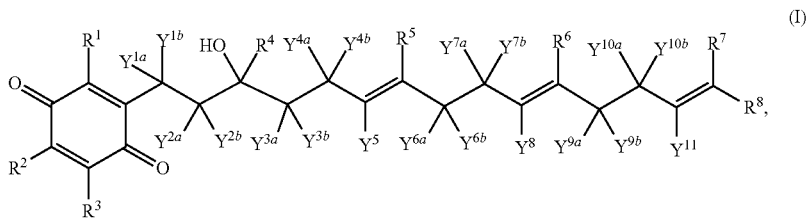

(I)

or a pharmaceutically acceptable salt thereof, wherein:

each of $R^1$, $R^2$, $R^3$, $R^4$, $R^5$, $R^6$, $R^7$ and $R^8$ is independently selected from —$CH_3$, —$CH_2D$, —$CHD_2$ and —$CD_3$;

each of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is independently selected from hydrogen and deuterium; and when each of $R^1$, $R^2$, $R^3$, $R^4$, $R^5$, $R^6$, $R^7$ and $R^8$ is —$CH_3$, then at least one of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is deuterium.

Certain aspects of the present invention further provide a compound of Formula II:

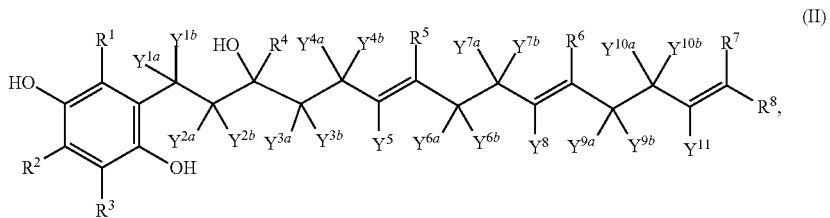

(II)

or a pharmaceutically acceptable salt thereof, wherein:

each of $R^1$, $R^2$, $R^3$, $R^4$, $R^5$, $R^6$, $R^7$ and $R^8$ is independently selected from —$CH_3$, —$CH_2D$, —$CHD_2$ and —$CD_3$;

each of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is independently selected from hydrogen and deuterium; and when each of $R^1$, $R^2$, $R^3$, $R^4$, $R^5$, $R^6$, $R^7$ and $R^8$ is —$CH_3$, then at least one of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is deuterium.

In some embodiments of the compound of Formula I, the stereochemistry at the hydroxy-substituted carbon atom is (R), the resulting compound having the Formula Ia:

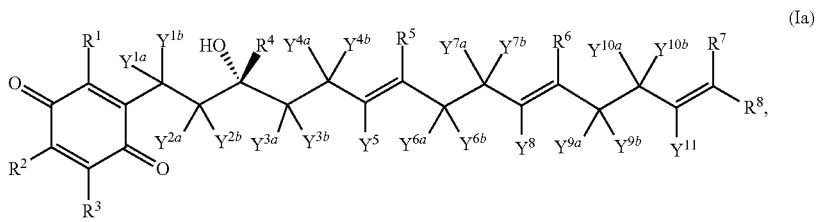

(Ia)

or a pharmaceutically acceptable salt thereof.

In some embodiments of the compound of Formula II, the stereochemistry at the hydroxy-substituted carbon atom is (R), the resulting compound having the Formula IIa:

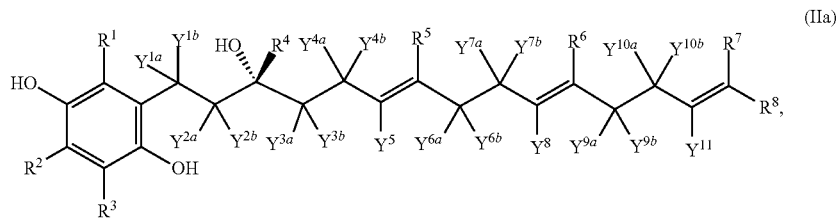

(IIa)

or a pharmaceutically acceptable salt thereof.

In some embodiments of Formulae I, Ia, II and IIa, each of $R^1$, $R^2$, $R^3$, $R^4$, $R^5$, $R^6$, $R^7$ and $R^8$ is independently selected from $—CH_3$ and $—CD_3$. In one aspect of these embodiments, $R^7$ and $R^8$ are $—CD_3$. In another aspect of these embodiments, $R^1$, $R^2$ and $R^3$ are the same. In a more specific aspect of these embodiments, $R^1$, $R^2$ and $R^3$ are $—CH_3$. In an alternate specific aspect of these embodiments, $R^1$, $R^2$ and $R^3$ are $—CD_3$. In an even more specific aspect of these embodiments, $R^7$ and $R^8$ are $—CD_3$; and $R^1$, $R^2$ and $R^3$ are the same. In another aspect of these embodiments, at least one of R and $R^6$ is $—CD_3$.

In some embodiments of Formulae I, Ia, II and IIa, $Y^{1a}$ and $Y^{1b}$ are the same.

In some embodiments of Formulae I, Ia, II and IIa, $Y^{2a}$ and $Y^{2b}$ are the same.

In some embodiments of Formulae I, Ia, II and IIa, $Y^{3a}$ and $Y^{3b}$ are the same.

In some embodiments of Formulae I, Ia, II and IIa, $Y^{4a}$ and $Y^{4b}$ are the same.

In some embodiments of Formulae I, Ia, II and IIa, $Y^{6a}$ and $Y^{6b}$ are the same.

In some embodiments of Formulae I, Ia, II and IIa, $Y^{7a}$ and $Y^{7b}$ are the same.

In some embodiments of Formulae I, Ia, II and IIa, $Y^{9a}$ and $Y^{9b}$ are the same.

In some embodiments of Formulae I, Ia, II and IIa, $Y^{10a}$ and $Y^{10b}$ are the same.

In some more specific embodiments of Formulae I, Ia, II and IIa, $Y^{1a}$ and $Y^{1b}$ are the same; $Y^{2a}$ and $Y^{2b}$ are the same; $Y^{3a}$ and $Y^{3b}$ are the same; $Y^{4a}$ and $Y^{4b}$ are the same; $Y^{6a}$ and $Y^{6b}$ are the same; $Y^{7a}$ and $Y^{7b}$ are the same; $Y^{9a}$ and $Y^{9b}$ are the same; and $Y^{10a}$ and $Y^{10b}$ are the same. In one aspect of these more specific embodiments, each of $R^1$, $R^2$, $R^3$, $R^4$, $R^5$, $R^6$, $R^7$ and $R^8$ is independently selected from $—CH_3$ and $—CD_3$. In another aspect of these more specific embodiments, each of $Y^{9a}$, $Y^{9b}$, $Y^{10a}$, $Y^{10b}$, and $Y^{11}$ is the same. In still another aspect of these more specific embodiments, each of $Y^{6a}$, $Y^{6b}$, $Y^{7a}$, $Y^{7b}$, and $Y^8$ is the same. In yet another aspect of these more specific embodiments, each of $Y^{3a}$, $Y^{3b}$, $Y^{4a}$, $Y^{4b}$, and $Y^5$ is the same. In another aspect of these more specific embodiments, each of $Y^{1a}$, $Y^{1b}$ $Y^{2a}$, and $Y^{2b}$ is the same.

In one embodiment of any of Formulae I, Ia, II or IIa, the invention does not include a compound wherein each of $R^1$, $R^2$, $R^3$, $R^4$, $R^5$, $R^6$, $R^7$ and $R^8$ is $—CD_3$, and each of $Y^{1a}$, $Y^{1b}$, $Y^{2a}$, $Y^{2b}$, $Y^{3a}$, $Y^{3b}$, $Y^{4a}$, $Y^{4b}$, $Y^5$, $Y^{6a}$, $Y^{6b}$, $Y^{7a}$, $Y^{7b}$, $Y^8$, $Y^{9a}$, $Y^{9b}$, $Y^{10a}$, $Y^{10b}$ and $Y^{11}$ is deuterium.

In another set of embodiments of Formulae I, Ia, II and IIa, any atom not designated as deuterium in any of the embodiments set forth above is present at its natural isotopic abundance.

In one embodiment of Formula Ia, $R^1$, $R^2$ and $R^3$ are the same; $R^7$ and $R^8$ are $—CD_3$; each of $Y^{1a}$, $Y^{1b}$, $Y^{2a}$, and $Y^{2b}$ is the same; each of $Y^{3a}$, $Y^{3b}$, $Y^{4a}$, $Y^{4b}$, and $Y^5$ is the same; each of $Y^{6a}$, $Y^{6b}$, $Y^{7a}$, $Y^{7b}$, and $Y^8$ is the same; each of $Y^{9a}$, $Y^{9b}$ $Y^{10a}$, $Y^{10b}$, and $Y^{11}$ is the same; and any atom not designated as deuterium is present at its natural isotopic abundance, wherein the compound is selected from any one of the compounds set forth in Table 1 (below):

TABLE 1

| | | | | | | | | |
|---|---|---|---|---|---|---|---|---|
| Exemplary Embodiments of Formula Ia | | | | | | | | |
| Compound # | $R^1/R^2/R^3$ | $R^4$ | $R^5$ | $R^6$ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
| 100 | $CD_3$ | $CH_3$ | $CH_3$ | $CH_3$ | H | H | H | H |
| 101 | $CH_3$ | $CD_3$ | $CH_3$ | $CH_3$ | H | H | H | H |
| 102 | $CH_3$ | $CH_3$ | $CD_3$ | $CH_3$ | H | H | H | H |
| 103 | $CH_3$ | $CH_3$ | $CH_3$ | $CD_3$ | H | H | H | H |
| 104 | $CD_3$ | $CD_3$ | $CH_3$ | $CH_3$ | H | H | H | H |
| 105 | $CD_3$ | $CH_3$ | $CD_3$ | $CH_3$ | H | H | H | H |
| 106 | $CD_3$ | $CH_3$ | $CH_3$ | $CD_3$ | H | H | H | H |
| 107 | $CH_3$ | $CD_3$ | $CD_3$ | $CH_3$ | H | H | H | H |
| 108 | $CH_3$ | $CD_3$ | $CH_3$ | $CD_3$ | H | H | H | H |
| 109 | $CH_3$ | $CH_3$ | $CD_3$ | $CD_3$ | H | H | H | H |
| 110 | $CD_3$ | $CD_3$ | $CD_3$ | $CH_3$ | H | H | H | H |
| 111 | $CD_3$ | $CD_3$ | $CH_3$ | $CD_3$ | H | H | H | H |
| 112 | $CD_3$ | $CH_3$ | $CD_3$ | $CD_3$ | H | H | H | H |
| 113 | $CH_3$ | $CD_3$ | $CD_3$ | $CD_3$ | H | H | H | H |
| 114 | $CD_3$ | $CD_3$ | $CD_3$ | $CD_3$ | H | H | H | H |
| 115 | $CD_3$ | $CH_3$ | $CH_3$ | $CH_3$ | D | H | H | H |
| 116 | $CH_3$ | $CD_3$ | $CH_3$ | $CH_3$ | D | H | H | H |
| 117 | $CH_3$ | $CH_3$ | $CD_3$ | $CH_3$ | D | H | H | H |

TABLE 1-continued

Exemplary Embodiments of Formula Ia

| Compound # | R¹/R²/R³ | R⁴ | R⁵ | R⁶ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 118 | CH₃ | CH₃ | CH₃ | CD₃ | D | H | H | H |
| 119 | CD₃ | CD₃ | CH₃ | CH₃ | D | H | H | H |
| 120 | CD₃ | CH₃ | CD₃ | CH₃ | D | H | H | H |
| 121 | CD₃ | CH₃ | CH₃ | CD₃ | D | H | H | H |
| 122 | CH₃ | CD₃ | CD₃ | CH₃ | D | H | H | H |
| 123 | CH₃ | CD₃ | CH₃ | CD₃ | D | H | H | H |
| 124 | CH₃ | CH₃ | CD₃ | CD₃ | D | H | H | H |
| 125 | CD₃ | CD₃ | CD₃ | CH₃ | D | H | H | H |
| 126 | CD₃ | CD₃ | CH₃ | CD₃ | D | H | H | H |
| 127 | CD₃ | CH₃ | CD₃ | CD₃ | D | H | H | H |
| 128 | CH₃ | CD₃ | CD₃ | CD₃ | D | H | H | H |
| 129 | CD₃ | CD₃ | CD₃ | CD₃ | D | H | H | H |
| 130 | CH₃ | CH₃ | CH₃ | CH₃ | D | H | H | H |
| 131 | CD₃ | CH₃ | CH₃ | CH₃ | H | D | H | H |
| 132 | CH₃ | CD₃ | CH₃ | CH₃ | H | D | H | H |
| 133 | CH₃ | CH₃ | CD₃ | CH₃ | H | D | H | H |
| 134 | CH₃ | CH₃ | CH₃ | CD₃ | H | D | H | H |
| 135 | CD₃ | CD₃ | CH₃ | CH₃ | H | D | H | H |
| 136 | CD₃ | CH₃ | CD₃ | CH₃ | H | D | H | H |
| 137 | CD₃ | CH₃ | CH₃ | CD₃ | H | D | H | H |
| 138 | CH₃ | CD₃ | CD₃ | CH₃ | H | D | H | H |
| 139 | CH₃ | CD₃ | CH₃ | CD₃ | H | D | H | H |
| 140 | CH₃ | CH₃ | CD₃ | CD₃ | H | D | H | H |
| 141 | CD₃ | CD₃ | CD₃ | CH₃ | H | D | H | H |
| 142 | CD₃ | CD₃ | CH₃ | CD₃ | H | D | H | H |
| 143 | CD₃ | CH₃ | CD₃ | CD₃ | H | D | H | H |
| 144 | CH₃ | CD₃ | CD₃ | CD₃ | H | D | H | H |
| 145 | CD₃ | CD₃ | CD₃ | CD₃ | H | D | H | H |
| 146 | CH₃ | CH₃ | CH₃ | CH₃ | H | D | H | H |
| 147 | CD₃ | CH₃ | CH₃ | CH₃ | H | H | D | H |
| 148 | CH₃ | CD₃ | CH₃ | CH₃ | H | H | D | H |
| 149 | CH₃ | CH₃ | CD₃ | CH₃ | H | H | D | H |
| 150 | CH₃ | CH₃ | CH₃ | CD₃ | H | H | D | H |
| 151 | CD₃ | CD₃ | CH₃ | CH₃ | H | H | D | H |
| 152 | CD₃ | CH₃ | CD₃ | CH₃ | H | H | D | H |
| 153 | CD₃ | CH₃ | CH₃ | CD₃ | H | H | D | H |
| 154 | CH₃ | CD₃ | CD₃ | CH₃ | H | H | D | H |
| 155 | CH₃ | CD₃ | CH₃ | CD₃ | H | H | D | H |
| 156 | CH₃ | CH₃ | CD₃ | CD₃ | H | H | D | H |
| 157 | CD₃ | CD₃ | CD₃ | CH₃ | H | H | D | H |
| 158 | CD₃ | CD₃ | CH₃ | CD₃ | H | H | D | H |
| 159 | CD₃ | CH₃ | CD₃ | CD₃ | H | H | D | H |
| 160 | CH₃ | CD₃ | CD₃ | CD₃ | H | H | D | H |
| 161 | CD₃ | CD₃ | CD₃ | CD₃ | H | H | D | H |
| 162 | CH₃ | CH₃ | CH₃ | CH₃ | H | H | D | H |
| 163 | CD₃ | CH₃ | CH₃ | CH₃ | H | H | H | D |
| 164 | CH₃ | CD₃ | CH₃ | CH₃ | H | H | H | D |
| 165 | CH₃ | CH₃ | CD₃ | CH₃ | H | H | H | D |
| 166 | CH₃ | CH₃ | CH₃ | CD₃ | H | H | H | D |
| 167 | CD₃ | CD₃ | CH₃ | CH₃ | H | H | H | D |
| 168 | CD₃ | CH₃ | CD₃ | CH₃ | H | H | H | D |
| 169 | CD₃ | CH₃ | CH₃ | CD₃ | H | H | H | D |
| 170 | CH₃ | CD₃ | CD₃ | CH₃ | H | H | H | D |
| 171 | CH₃ | CD₃ | CH₃ | CD₃ | H | H | H | D |
| 172 | CH₃ | CH₃ | CD₃ | CD₃ | H | H | H | D |
| 173 | CD₃ | CD₃ | CD₃ | CH₃ | H | H | H | D |
| 174 | CD₃ | CD₃ | CH₃ | CD₃ | H | H | H | D |
| 175 | CD₃ | CH₃ | CD₃ | CD₃ | H | H | H | D |
| 176 | CH₃ | CD₃ | CD₃ | CD₃ | H | H | H | D |
| 177 | CD₃ | CD₃ | CD₃ | CD₃ | H | H | H | D |
| 178 | CH₃ | CH₃ | CH₃ | CH₃ | H | H | H | D |
| 179 | CD₃ | CH₃ | CH₃ | CH₃ | D | D | H | H |
| 180 | CH₃ | CD₃ | CH₃ | CH₃ | D | D | H | H |
| 181 | CH₃ | CH₃ | CD₃ | CH₃ | D | D | H | H |
| 182 | CH₃ | CH₃ | CH₃ | CD₃ | D | D | H | H |
| 183 | CD₃ | CD₃ | CH₃ | CH₃ | D | D | H | H |
| 184 | CD₃ | CH₃ | CD₃ | CH₃ | D | D | H | H |
| 185 | CD₃ | CH₃ | CH₃ | CD₃ | D | D | H | H |
| 186 | CH₃ | CD₃ | CD₃ | CH₃ | D | D | H | H |
| 187 | CH₃ | CD₃ | CH₃ | CD₃ | D | D | H | H |
| 188 | CH₃ | CH₃ | CD₃ | CD₃ | D | D | H | H |
| 189 | CD₃ | CD₃ | CD₃ | CH₃ | D | D | H | H |
| 190 | CD₃ | CD₃ | CH₃ | CD₃ | D | D | H | H |
| 191 | CD₃ | CH₃ | CD₃ | CD₃ | D | D | H | H |
| 192 | CH₃ | CD₃ | CD₃ | CD₃ | D | D | H | H |

TABLE 1-continued

Exemplary Embodiments of Formula Ia

| Compound # | R¹/R²/R³ | R⁴ | R⁵ | R⁶ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 193 | CD₃ | CD₃ | CD₃ | CD₃ | D | D | H | H |
| 194 | CH₃ | CH₃ | CH₃ | CH₃ | D | D | H | H |
| 195 | CD₃ | CH₃ | CH₃ | CH₃ | D | H | D | H |
| 196 | CH₃ | CD₃ | CH₃ | CH₃ | D | H | D | H |
| 197 | CH₃ | CH₃ | CD₃ | CH₃ | D | H | D | H |
| 198 | CH₃ | CH₃ | CH₃ | CD₃ | D | H | D | H |
| 199 | CD₃ | CD₃ | CH₃ | CH₃ | D | H | D | H |
| 200 | CD₃ | CH₃ | CD₃ | CH₃ | D | H | D | H |
| 201 | CD₃ | CH₃ | CH₃ | CD₃ | D | H | D | H |
| 202 | CH₃ | CD₃ | CD₃ | CH₃ | D | H | D | H |
| 203 | CH₃ | CD₃ | CH₃ | CD₃ | D | H | D | H |
| 204 | CH₃ | CH₃ | CD₃ | CD₃ | D | H | D | H |
| 205 | CD₃ | CD₃ | CD₃ | CH₃ | D | H | D | H |
| 206 | CD₃ | CD₃ | CH₃ | CD₃ | D | H | D | H |
| 207 | CD₃ | CH₃ | CD₃ | CD₃ | D | H | D | H |
| 208 | CH₃ | CD₃ | CD₃ | CD₃ | D | H | D | H |
| 209 | CD₃ | CD₃ | CD₃ | CD₃ | D | H | D | H |
| 210 | CH₃ | CH₃ | CH₃ | CH₃ | D | H | D | H |
| 211 | CD₃ | CH₃ | CH₃ | CH₃ | D | H | H | D |
| 212 | CH₃ | CD₃ | CH₃ | CH₃ | D | H | H | D |
| 213 | CH₃ | CH₃ | CD₃ | CH₃ | D | H | H | D |
| 214 | CH₃ | CH₃ | CH₃ | CD₃ | D | H | H | D |
| 215 | CD₃ | CD₃ | CH₃ | CH₃ | D | H | H | D |
| 216 | CD₃ | CH₃ | CD₃ | CH₃ | D | H | H | D |
| 217 | CD₃ | CH₃ | CH₃ | CD₃ | D | H | H | D |
| 218 | CH₃ | CD₃ | CD₃ | CH₃ | D | H | H | D |
| 219 | CH₃ | CD₃ | CH₃ | CD₃ | D | H | H | D |
| 220 | CH₃ | CH₃ | CD₃ | CD₃ | D | H | H | D |
| 221 | CD₃ | CD₃ | CD₃ | CH₃ | D | H | H | D |
| 222 | CD₃ | CD₃ | CH₃ | CD₃ | D | H | H | D |
| 223 | CD₃ | CH₃ | CD₃ | CD₃ | D | H | H | D |
| 224 | CH₃ | CD₃ | CD₃ | CD₃ | D | H | H | D |
| 225 | CD₃ | CD₃ | CD₃ | CD₃ | D | H | H | D |
| 226 | CH₃ | CH₃ | CH₃ | CH₃ | D | H | H | D |
| 227 | CD₃ | CH₃ | CH₃ | CH₃ | H | D | D | H |
| 228 | CH₃ | CD₃ | CH₃ | CH₃ | H | D | D | H |
| 229 | CH₃ | CH₃ | CD₃ | CH₃ | H | D | D | H |
| 230 | CH₃ | CH₃ | CH₃ | CD₃ | H | D | D | H |
| 231 | CD₃ | CD₃ | CH₃ | CH₃ | H | D | D | H |
| 232 | CD₃ | CH₃ | CD₃ | CH₃ | H | D | D | H |
| 233 | CD₃ | CH₃ | CH₃ | CD₃ | H | D | D | H |
| 234 | CH₃ | CD₃ | CD₃ | CH₃ | H | D | D | H |
| 235 | CH₃ | CD₃ | CH₃ | CD₃ | H | D | D | H |
| 236 | CH₃ | CH₃ | CD₃ | CD₃ | H | D | D | H |
| 237 | CD₃ | CD₃ | CD₃ | CH₃ | H | D | D | H |
| 238 | CD₃ | CD₃ | CH₃ | CD₃ | H | D | D | H |
| 239 | CD₃ | CH₃ | CD₃ | CD₃ | H | D | D | H |
| 240 | CH₃ | CD₃ | CD₃ | CD₃ | H | D | D | H |
| 241 | CD₃ | CD₃ | CD₃ | CD₃ | H | D | D | H |
| 242 | CH₃ | CH₃ | CH₃ | CH₃ | H | D | D | H |
| 243 | CD₃ | CH₃ | CH₃ | CH₃ | H | D | H | D |
| 244 | CH₃ | CD₃ | CH₃ | CH₃ | H | D | H | D |
| 245 | CH₃ | CH₃ | CD₃ | CH₃ | H | D | H | D |
| 246 | CH₃ | CH₃ | CH₃ | CD₃ | H | D | H | D |
| 247 | CD₃ | CD₃ | CH₃ | CH₃ | H | D | H | D |
| 248 | CD₃ | CH₃ | CD₃ | CH₃ | H | D | H | D |
| 249 | CD₃ | CH₃ | CH₃ | CD₃ | H | D | H | D |
| 250 | CH₃ | CD₃ | CD₃ | CH₃ | H | D | H | D |
| 251 | CH₃ | CD₃ | CH₃ | CD₃ | H | D | H | D |
| 252 | CH₃ | CH₃ | CD₃ | CD₃ | H | D | H | D |
| 253 | CD₃ | CD₃ | CD₃ | CH₃ | H | D | H | D |
| 254 | CD₃ | CD₃ | CH₃ | CD₃ | H | D | H | D |
| 255 | CD₃ | CH₃ | CD₃ | CD₃ | H | D | H | D |
| 256 | CH₃ | CD₃ | CD₃ | CD₃ | H | D | H | D |
| 257 | CD₃ | CD₃ | CD₃ | CD₃ | H | D | H | D |
| 258 | CH₃ | CH₃ | CH₃ | CH₃ | H | D | H | D |
| 259 | CD₃ | CH₃ | CH₃ | CH₃ | H | H | D | D |
| 260 | CH₃ | CD₃ | CH₃ | CH₃ | H | H | D | D |
| 261 | CH₃ | CH₃ | CD₃ | CH₃ | H | H | D | D |
| 262 | CH₃ | CH₃ | CH₃ | CD₃ | H | H | D | D |
| 263 | CD₃ | CD₃ | CH₃ | CH₃ | H | H | D | D |
| 264 | CD₃ | CH₃ | CD₃ | CH₃ | H | H | D | D |
| 265 | CD₃ | CH₃ | CH₃ | CD₃ | H | H | D | D |
| 266 | CH₃ | CD₃ | CD₃ | CH₃ | H | H | D | D |
| 267 | CH₃ | CD₃ | CH₃ | CD₃ | H | H | D | D |

TABLE 1-continued

Exemplary Embodiments of Formula Ia

| Compound # | R$^1$/R$^2$/R$^3$ | R$^4$ | R$^5$ | R$^6$ | Y$^{1a}$/Y$^{1b}$/Y$^{2a}$/Y$^{2b}$ | Y$^{3a}$/Y$^{3b}$/Y$^{4a}$/Y$^{4b}$/Y$^5$ | Y$^{6a}$/Y$^{6b}$/Y$^{7a}$/Y$^{7b}$/Y$^8$ | Y$^{9a}$/Y$^{9b}$/Y$^{10a}$/Y$^{10b}$/Y$^{11}$ |
|---|---|---|---|---|---|---|---|---|
| 268 | CH$_3$ | CH$_3$ | CD$_3$ | CD$_3$ | H | H | D | D |
| 269 | CD$_3$ | CD$_3$ | CD$_3$ | CH$_3$ | H | H | D | D |
| 270 | CD$_3$ | CD$_3$ | CH$_3$ | CD$_3$ | H | H | D | D |
| 271 | CD$_3$ | CH$_3$ | CD$_3$ | CD$_3$ | H | H | D | D |
| 272 | CH$_3$ | CD$_3$ | CD$_3$ | CD$_3$ | H | H | D | D |
| 273 | CD$_3$ | CD$_3$ | CD$_3$ | CD$_3$ | H | H | D | D |
| 274 | CH$_3$ | CH$_3$ | CH$_3$ | CH$_3$ | H | H | D | D |
| 275 | CD$_3$ | CH$_3$ | CH$_3$ | CH$_3$ | D | D | D | H |
| 276 | CH$_3$ | CD$_3$ | CH$_3$ | CH$_3$ | D | D | D | H |
| 277 | CH$_3$ | CH$_3$ | CD$_3$ | CH$_3$ | D | D | D | H |
| 278 | CH$_3$ | CH$_3$ | CH$_3$ | CD$_3$ | D | D | D | H |
| 279 | CD$_3$ | CD$_3$ | CH$_3$ | CH$_3$ | D | D | D | H |
| 280 | CD$_3$ | CH$_3$ | CD$_3$ | CH$_3$ | D | D | D | H |
| 281 | CD$_3$ | CH$_3$ | CH$_3$ | CD$_3$ | D | D | D | H |
| 282 | CH$_3$ | CD$_3$ | CD$_3$ | CH$_3$ | D | D | D | H |
| 283 | CH$_3$ | CD$_3$ | CH$_3$ | CD$_3$ | D | D | D | H |
| 284 | CH$_3$ | CH$_3$ | CD$_3$ | CD$_3$ | D | D | D | H |
| 285 | CD$_3$ | CD$_3$ | CD$_3$ | CH$_3$ | D | D | D | H |
| 286 | CD$_3$ | CD$_3$ | CH$_3$ | CD$_3$ | D | D | D | H |
| 287 | CD$_3$ | CH$_3$ | CD$_3$ | CD$_3$ | D | D | D | H |
| 288 | CH$_3$ | CD$_3$ | CD$_3$ | CD$_3$ | D | D | D | H |
| 289 | CD$_3$ | CD$_3$ | CD$_3$ | CD$_3$ | D | D | D | H |
| 290 | CH$_3$ | CH$_3$ | CH$_3$ | CH$_3$ | D | D | D | H |
| 291 | CD$_3$ | CH$_3$ | CH$_3$ | CH$_3$ | D | D | H | D |
| 292 | CH$_3$ | CD$_3$ | CH$_3$ | CH$_3$ | D | D | H | D |
| 293 | CH$_3$ | CH$_3$ | CD$_3$ | CH$_3$ | D | D | H | D |
| 294 | CH$_3$ | CH$_3$ | CH$_3$ | CD$_3$ | D | D | H | D |
| 295 | CD$_3$ | CD$_3$ | CH$_3$ | CH$_3$ | D | D | H | D |
| 296 | CD$_3$ | CH$_3$ | CD$_3$ | CH$_3$ | D | D | H | D |
| 297 | CD$_3$ | CH$_3$ | CH$_3$ | CD$_3$ | D | D | H | D |
| 298 | CH$_3$ | CD$_3$ | CD$_3$ | CH$_3$ | D | D | H | D |
| 299 | CH$_3$ | CD$_3$ | CH$_3$ | CD$_3$ | D | D | H | D |
| 300 | CH$_3$ | CH$_3$ | CD$_3$ | CD$_3$ | D | D | H | D |
| 301 | CD$_3$ | CD$_3$ | CD$_3$ | CH$_3$ | D | D | H | D |
| 302 | CD$_3$ | CD$_3$ | CH$_3$ | CD$_3$ | D | D | H | D |
| 303 | CD$_3$ | CH$_3$ | CD$_3$ | CD$_3$ | D | D | H | D |
| 304 | CH$_3$ | CD$_3$ | CD$_3$ | CD$_3$ | D | D | H | D |
| 305 | CD$_3$ | CD$_3$ | CD$_3$ | CD$_3$ | D | D | H | D |
| 306 | CH$_3$ | CH$_3$ | CH$_3$ | CH$_3$ | D | D | H | D |
| 307 | CD$_3$ | CH$_3$ | CH$_3$ | CH$_3$ | D | H | D | D |
| 308 | CH$_3$ | CD$_3$ | CH$_3$ | CH$_3$ | D | H | D | D |
| 309 | CH$_3$ | CH$_3$ | CD$_3$ | CH$_3$ | D | H | D | D |
| 310 | CH$_3$ | CH$_3$ | CH$_3$ | CD$_3$ | D | H | D | D |
| 311 | CD$_3$ | CD$_3$ | CH$_3$ | CH$_3$ | D | H | D | D |
| 312 | CD$_3$ | CH$_3$ | CD$_3$ | CH$_3$ | D | H | D | D |
| 313 | CD$_3$ | CH$_3$ | CH$_3$ | CD$_3$ | D | H | D | D |
| 314 | CH$_3$ | CD$_3$ | CD$_3$ | CH$_3$ | D | H | D | D |
| 315 | CH$_3$ | CD$_3$ | CH$_3$ | CD$_3$ | D | H | D | D |
| 316 | CH$_3$ | CH$_3$ | CD$_3$ | CD$_3$ | D | H | D | D |
| 317 | CD$_3$ | CD$_3$ | CD$_3$ | CH$_3$ | D | H | D | D |
| 318 | CD$_3$ | CD$_3$ | CH$_3$ | CD$_3$ | D | H | D | D |
| 319 | CD$_3$ | CH$_3$ | CD$_3$ | CD$_3$ | D | H | D | D |
| 320 | CH$_3$ | CD$_3$ | CD$_3$ | CD$_3$ | D | H | D | D |
| 321 | CD$_3$ | CD$_3$ | CD$_3$ | CD$_3$ | D | H | D | D |
| 322 | CH$_3$ | CH$_3$ | CH$_3$ | CH$_3$ | D | H | D | D |
| 323 | CD$_3$ | CH$_3$ | CH$_3$ | CH$_3$ | H | D | D | D |
| 324 | CH$_3$ | CD$_3$ | CH$_3$ | CH$_3$ | H | D | D | D |
| 325 | CH$_3$ | CH$_3$ | CD$_3$ | CH$_3$ | H | D | D | D |
| 326 | CH$_3$ | CH$_3$ | CH$_3$ | CD$_3$ | H | D | D | D |
| 327 | CD$_3$ | CD$_3$ | CH$_3$ | CH$_3$ | H | D | D | D |
| 328 | CD$_3$ | CH$_3$ | CD$_3$ | CH$_3$ | H | D | D | D |
| 329 | CD$_3$ | CH$_3$ | CH$_3$ | CD$_3$ | H | D | D | D |
| 330 | CH$_3$ | CD$_3$ | CD$_3$ | CH$_3$ | H | D | D | D |
| 331 | CH$_3$ | CD$_3$ | CH$_3$ | CD$_3$ | H | D | D | D |
| 332 | CH$_3$ | CH$_3$ | CD$_3$ | CD$_3$ | H | D | D | D |
| 333 | CD$_3$ | CD$_3$ | CD$_3$ | CH$_3$ | H | D | D | D |
| 334 | CD$_3$ | CD$_3$ | CH$_3$ | CD$_3$ | H | D | D | D |
| 335 | CD$_3$ | CH$_3$ | CD$_3$ | CD$_3$ | H | D | D | D |
| 336 | CH$_3$ | CD$_3$ | CD$_3$ | CD$_3$ | H | D | D | D |
| 337 | CD$_3$ | CD$_3$ | CD$_3$ | CD$_3$ | H | D | D | D |
| 338 | CH$_3$ | CH$_3$ | CH$_3$ | CH$_3$ | H | D | D | D |
| 339 | CD$_3$ | CH$_3$ | CH$_3$ | CH$_3$ | D | D | D | D |
| 340 | CH$_3$ | CD$_3$ | CH$_3$ | CH$_3$ | D | D | D | D |
| 341 | CH$_3$ | CH$_3$ | CD$_3$ | CH$_3$ | D | D | D | D |
| 342 | CH$_3$ | CH$_3$ | CH$_3$ | CD$_3$ | D | D | D | D |

TABLE 1-continued

Exemplary Embodiments of Formula Ia

| Compound # | $R^1/R^2/R^3$ | $R^4$ | $R^5$ | $R^6$ | $Y^{1a}/Y^{1b}/$ $Y^{2a}/Y^{2b}$ | $Y^{3a}/Y^{3b}/$ $Y^{4a}/Y^{4b}/Y^5$ | $Y^{6a}/Y^{6b}/$ $Y^{7a}/Y^{7b}/Y^8$ | $Y^{9a}/Y^{9b}/$ $Y^{10a}/Y^{10b}/Y^{11}$ |
|---|---|---|---|---|---|---|---|---|
| 343 | $CD_3$ | $CD_3$ | $CH_3$ | $CH_3$ | D | D | D | D |
| 344 | $CD_3$ | $CH_3$ | $CD_3$ | $CH_3$ | D | D | D | D |
| 345 | $CD_3$ | $CH_3$ | $CH_3$ | $CD_3$ | D | D | D | D |
| 346 | $CH_3$ | $CD_3$ | $CD_3$ | $CH_3$ | D | D | D | D |
| 347 | $CH_3$ | $CD_3$ | $CH_3$ | $CD_3$ | D | D | D | D |
| 348 | $CH_3$ | $CH_3$ | $CD_3$ | $CD_3$ | D | D | D | D |
| 349 | $CD_3$ | $CD_3$ | $CD_3$ | $CH_3$ | D | D | D | D |
| 350 | $CD_3$ | $CD_3$ | $CH_3$ | $CD_3$ | D | D | D | D |
| 351 | $CD_3$ | $CH_3$ | $CD_3$ | $CD_3$ | D | D | D | D |
| 352 | $CH_3$ | $CD_3$ | $CD_3$ | $CD_3$ | D | D | D | D |
| 353 | $CD_3$ | $CD_3$ | $CD_3$ | $CD_3$ | D | D | D | D |
| 354 | $CH_3$ | $CH_3$ | $CH_3$ | $CH_3$ | D | D | D | D |
| 355 | $CH_3$ | $CH_3$ | $CH_3$ | $CH_3$ | H | H | H | H | or a pharmaceutically acceptable salt thereof.

In another embodiment, the compound of the invention is selected from:

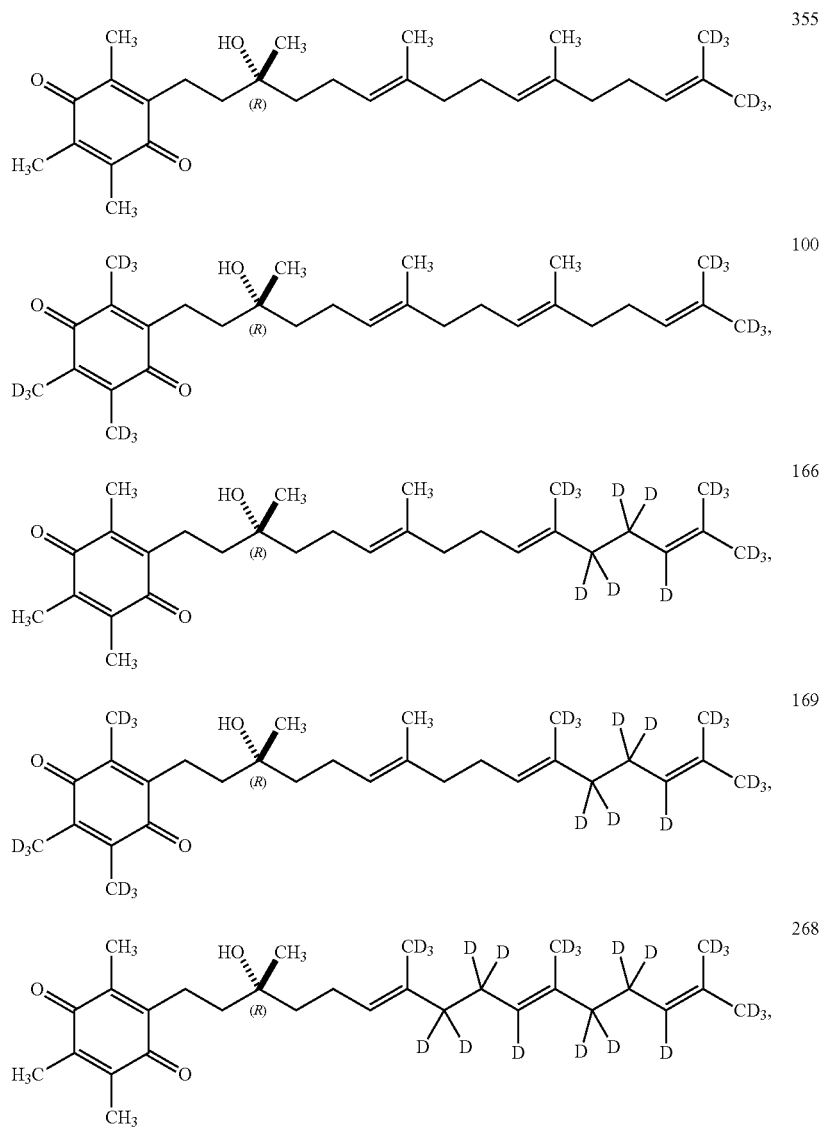

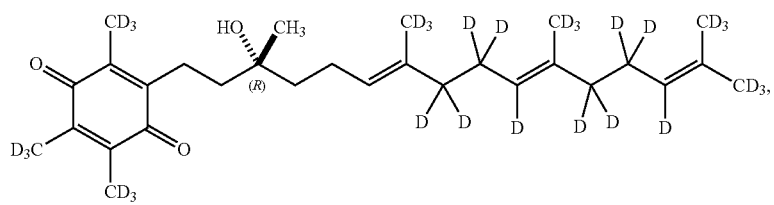
271
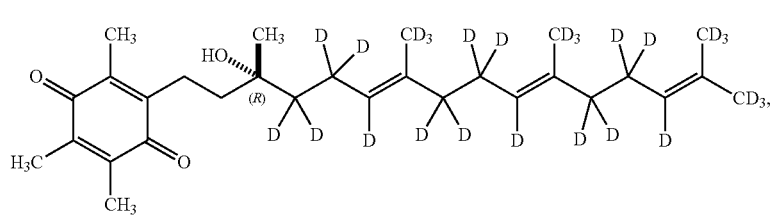
332
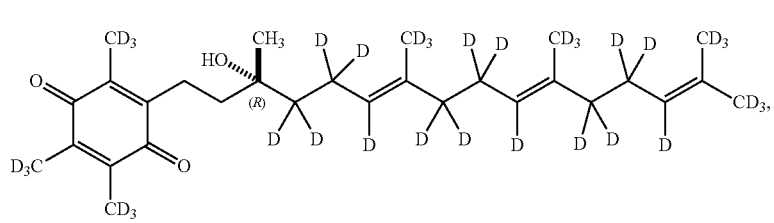
335
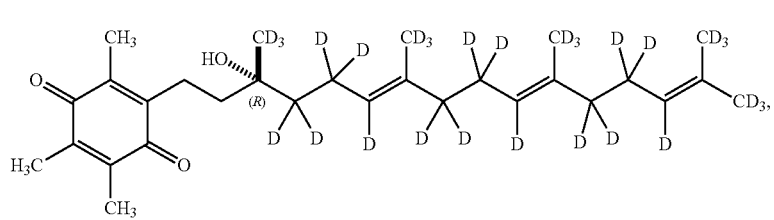
336
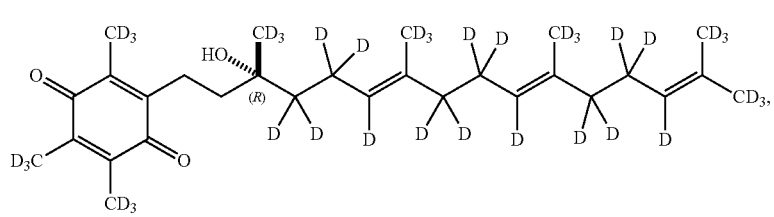
337
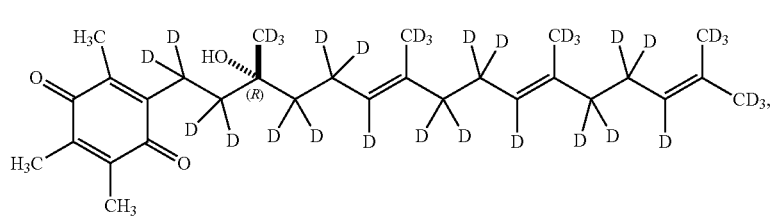
352
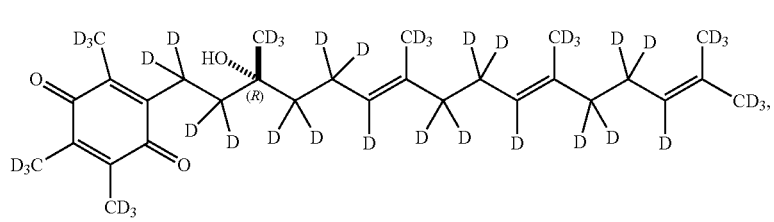
353

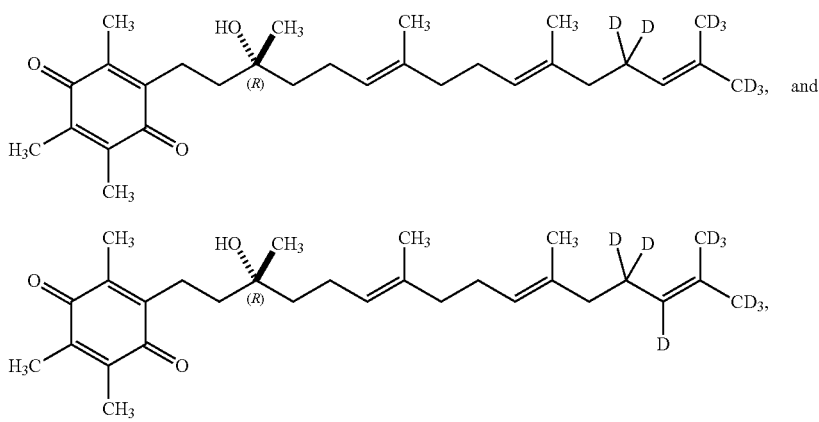

or a pharmaceutically acceptable salt thereof.

In one embodiment of Formula IIa, $R^1$, $R^2$ and $R^3$ are the same; $R^7$ and $R^8$ are —$CD_3$; each of $Y^{1a}$, $Y^{1b}$, $Y^{2a}$, and $Y^{2b}$ is the same; each of $Y^{3a}$, $Y^{3b}$, $Y^{4a}$, $Y^{4b}$, and $Y^5$ is the same; each of $Y^{6a}$, $Y^{6b}$, $Y^{7a}$, $Y^{7b}$, and $Y^8$ is the same; each of $Y^{9a}$, $Y^{9b}$, $Y^{10a}$, $Y^{10b}$, and $Y^{11}$ is the same; and any atom not designated as deuterium is present at its natural isotopic abundance, wherein the compound is selected from any one of the compounds set forth in Table 2 (below):

TABLE 2

Exemplary Embodiments of Formula IIa

| Compound # | $R^1/R^2/R^3$ | $R^4$ | $R^5$ | $R^6$ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 100a | $CD_3$ | $CH_3$ | $CH_3$ | $CH_3$ | H | H | H | H |
| 101a | $CH_3$ | $CD_3$ | $CH_3$ | $CH_3$ | H | H | H | H |
| 102a | $CH_3$ | $CH_3$ | $CD_3$ | $CH_3$ | H | H | H | H |
| 103a | $CH_3$ | $CH_3$ | $CH_3$ | $CD_3$ | H | H | H | H |
| 104a | $CD_3$ | $CD_3$ | $CH_3$ | $CH_3$ | H | H | H | H |
| 105a | $CD_3$ | $CH_3$ | $CD_3$ | $CH_3$ | H | H | H | H |
| 106a | $CD_3$ | $CH_3$ | $CH_3$ | $CD_3$ | H | H | H | H |
| 107a | $CH_3$ | $CD_3$ | $CD_3$ | $CH_3$ | H | H | H | H |
| 108a | $CH_3$ | $CD_3$ | $CH_3$ | $CD_3$ | H | H | H | H |
| 109a | $CH_3$ | $CH_3$ | $CD_3$ | $CD_3$ | H | H | H | H |
| 110a | $CD_3$ | $CD_3$ | $CD_3$ | $CH_3$ | H | H | H | H |
| 111a | $CD_3$ | $CD_3$ | $CH_3$ | $CD_3$ | H | H | H | H |
| 112a | $CD_3$ | $CH_3$ | $CD_3$ | $CD_3$ | H | H | H | H |
| 113a | $CH_3$ | $CD_3$ | $CD_3$ | $CD_3$ | H | H | H | H |
| 114a | $CD_3$ | $CD_3$ | $CD_3$ | $CD_3$ | H | H | H | H |
| 115a | $CD_3$ | $CH_3$ | $CH_3$ | $CH_3$ | D | H | H | H |
| 116a | $CH_3$ | $CD_3$ | $CH_3$ | $CH_3$ | D | H | H | H |
| 117a | $CH_3$ | $CH_3$ | $CD_3$ | $CH_3$ | D | H | H | H |
| 118a | $CH_3$ | $CH_3$ | $CH_3$ | $CD_3$ | D | H | H | H |
| 119a | $CD_3$ | $CD_3$ | $CH_3$ | $CH_3$ | D | H | H | H |
| 120a | $CD_3$ | $CH_3$ | $CD_3$ | $CH_3$ | D | H | H | H |
| 121a | $CD_3$ | $CH_3$ | $CH_3$ | $CD_3$ | D | H | H | H |
| 122a | $CH_3$ | $CD_3$ | $CD_3$ | $CH_3$ | D | H | H | H |
| 123a | $CH_3$ | $CD_3$ | $CH_3$ | $CD_3$ | D | H | H | H |
| 124a | $CH_3$ | $CH_3$ | $CD_3$ | $CD_3$ | D | H | H | H |
| 125a | $CD_3$ | $CD_3$ | $CD_3$ | $CH_3$ | D | H | H | H |
| 126a | $CD_3$ | $CD_3$ | $CH_3$ | $CD_3$ | D | H | H | H |
| 127a | $CD_3$ | $CH_3$ | $CD_3$ | $CD_3$ | D | H | H | H |
| 128a | $CH_3$ | $CD_3$ | $CD_3$ | $CD_3$ | D | H | H | H |
| 129a | $CD_3$ | $CD_3$ | $CD_3$ | $CD_3$ | D | H | H | H |
| 130a | $CH_3$ | $CH_3$ | $CH_3$ | $CH_3$ | D | H | H | H |
| 131a | $CD_3$ | $CH_3$ | $CH_3$ | $CH_3$ | H | D | H | H |
| 132a | $CH_3$ | $CD_3$ | $CH_3$ | $CH_3$ | H | D | H | H |
| 133a | $CH_3$ | $CH_3$ | $CD_3$ | $CH_3$ | H | D | H | H |
| 134a | $CH_3$ | $CH_3$ | $CH_3$ | $CD_3$ | H | D | H | H |
| 135a | $CD_3$ | $CD_3$ | $CH_3$ | $CH_3$ | H | D | H | H |
| 136a | $CD_3$ | $CH_3$ | $CD_3$ | $CH_3$ | H | D | H | H |
| 137a | $CD_3$ | $CH_3$ | $CH_3$ | $CD_3$ | H | D | H | H |
| 138a | $CH_3$ | $CD_3$ | $CD_3$ | $CH_3$ | H | D | H | H |
| 139a | $CH_3$ | $CD_3$ | $CH_3$ | $CD_3$ | H | D | H | H |
| 140a | $CH_3$ | $CH_3$ | $CD_3$ | $CD_3$ | H | D | H | H |
| 141a | $CD_3$ | $CD_3$ | $CD_3$ | $CH_3$ | H | D | H | H |
| 142a | $CD_3$ | $CD_3$ | $CH_3$ | $CD_3$ | H | D | H | H |

TABLE 2-continued

Exemplary Embodiments of Formula IIa

| Compound # | R¹/R²/R³ | R⁴ | R⁵ | R⁶ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 143a | CD₃ | CH₃ | CD₃ | CD₃ | H | D | H | H |
| 144a | CH₃ | CD₃ | CD₃ | CD₃ | H | D | H | H |
| 145a | CD₃ | CD₃ | CD₃ | CD₃ | H | D | H | H |
| 146a | CH₃ | CH₃ | CH₃ | CH₃ | H | D | H | H |
| 147a | CD₃ | CH₃ | CH₃ | CH₃ | H | H | D | H |
| 148a | CH₃ | CD₃ | CH₃ | CH₃ | H | H | D | H |
| 149a | CH₃ | CH₃ | CD₃ | CH₃ | H | H | D | H |
| 150a | CH₃ | CH₃ | CH₃ | CD₃ | H | H | D | H |
| 151a | CD₃ | CD₃ | CH₃ | CH₃ | H | H | D | H |
| 152a | CD₃ | CH₃ | CD₃ | CH₃ | H | H | D | H |
| 153a | CD₃ | CH₃ | CH₃ | CD₃ | H | H | D | H |
| 154a | CH₃ | CD₃ | CD₃ | CH₃ | H | H | D | H |
| 155a | CH₃ | CD₃ | CH₃ | CD₃ | H | H | D | H |
| 156a | CH₃ | CH₃ | CD₃ | CD₃ | H | H | D | H |
| 157a | CD₃ | CD₃ | CD₃ | CH₃ | H | H | D | H |
| 158a | CD₃ | CD₃ | CH₃ | CD₃ | H | H | D | H |
| 159a | CD₃ | CH₃ | CD₃ | CD₃ | H | H | D | H |
| 160a | CH₃ | CD₃ | CD₃ | CD₃ | H | H | D | H |
| 161a | CD₃ | CD₃ | CD₃ | CD₃ | H | H | D | H |
| 162a | CH₃ | CH₃ | CH₃ | CH₃ | H | H | D | H |
| 163a | CD₃ | CH₃ | CH₃ | CH₃ | H | H | H | D |
| 164a | CH₃ | CD₃ | CH₃ | CH₃ | H | H | H | D |
| 165a | CH₃ | CH₃ | CD₃ | CH₃ | H | H | H | D |
| 166a | CH₃ | CH₃ | CH₃ | CD₃ | H | H | H | D |
| 167a | CD₃ | CD₃ | CH₃ | CH₃ | H | H | H | D |
| 168a | CD₃ | CH₃ | CD₃ | CH₃ | H | H | H | D |
| 169a | CD₃ | CH₃ | CH₃ | CD₃ | H | H | H | D |
| 170a | CH₃ | CD₃ | CD₃ | CH₃ | H | H | H | D |
| 171a | CH₃ | CD₃ | CH₃ | CD₃ | H | H | H | D |
| 172a | CH₃ | CH₃ | CD₃ | CD₃ | H | H | H | D |
| 173a | CD₃ | CD₃ | CD₃ | CH₃ | H | H | H | D |
| 174a | CD₃ | CD₃ | CH₃ | CD₃ | H | H | H | D |
| 175a | CD₃ | CH₃ | CD₃ | CD₃ | H | H | H | D |
| 176a | CH₃ | CD₃ | CD₃ | CD₃ | H | H | H | D |
| 177a | CD₃ | CD₃ | CD₃ | CD₃ | H | H | H | D |
| 178a | CH₃ | CH₃ | CH₃ | CH₃ | H | H | H | D |
| 179a | CD₃ | CH₃ | CH₃ | CH₃ | D | D | H | H |
| 180a | CH₃ | CD₃ | CH₃ | CH₃ | D | D | H | H |
| 181a | CH₃ | CH₃ | CD₃ | CH₃ | D | D | H | H |
| 182a | CH₃ | CH₃ | CH₃ | CD₃ | D | D | H | H |
| 183a | CD₃ | CD₃ | CH₃ | CH₃ | D | D | H | H |
| 184a | CD₃ | CH₃ | CD₃ | CH₃ | D | D | H | H |
| 185a | CD₃ | CH₃ | CH₃ | CD₃ | D | D | H | H |
| 186a | CH₃ | CD₃ | CD₃ | CH₃ | D | D | H | H |
| 187a | CH₃ | CD₃ | CH₃ | CD₃ | D | D | H | H |
| 188a | CH₃ | CH₃ | CD₃ | CD₃ | D | D | H | H |
| 189a | CD₃ | CD₃ | CD₃ | CH₃ | D | D | H | H |
| 190a | CD₃ | CD₃ | CH₃ | CD₃ | D | D | H | H |
| 191a | CD₃ | CH₃ | CD₃ | CD₃ | D | D | H | H |
| 192a | CH₃ | CD₃ | CD₃ | CD₃ | D | D | H | H |
| 193a | CD₃ | CD₃ | CD₃ | CD₃ | D | D | H | H |
| 194a | CH₃ | CH₃ | CH₃ | CH₃ | D | D | H | H |
| 195a | CD₃ | CH₃ | CH₃ | CH₃ | D | H | D | H |
| 196a | CH₃ | CD₃ | CH₃ | CH₃ | D | H | D | H |
| 197a | CH₃ | CH₃ | CD₃ | CH₃ | D | H | D | H |
| 198a | CH₃ | CH₃ | CH₃ | CD₃ | D | H | D | H |
| 199a | CD₃ | CD₃ | CH₃ | CH₃ | D | H | D | H |
| 200a | CD₃ | CH₃ | CD₃ | CH₃ | D | H | D | H |
| 201a | CD₃ | CH₃ | CH₃ | CD₃ | D | H | D | H |
| 202a | CH₃ | CD₃ | CD₃ | CH₃ | D | H | D | H |
| 203a | CH₃ | CD₃ | CH₃ | CD₃ | D | H | D | H |
| 204a | CH₃ | CH₃ | CD₃ | CD₃ | D | H | D | H |
| 205a | CD₃ | CD₃ | CD₃ | CH₃ | D | H | D | H |
| 206a | CD₃ | CD₃ | CH₃ | CD₃ | D | H | D | H |
| 207a | CD₃ | CH₃ | CD₃ | CD₃ | D | H | D | H |
| 208a | CH₃ | CD₃ | CD₃ | CD₃ | D | H | D | H |
| 209a | CD₃ | CD₃ | CD₃ | CD₃ | D | H | D | H |
| 210a | CH₃ | CH₃ | CH₃ | CH₃ | D | H | D | H |
| 211a | CD₃ | CH₃ | CH₃ | CH₃ | D | H | H | D |
| 212a | CH₃ | CD₃ | CH₃ | CH₃ | D | H | H | D |
| 213a | CH₃ | CH₃ | CD₃ | CH₃ | D | H | H | D |
| 214a | CH₃ | CH₃ | CH₃ | CD₃ | D | H | H | D |
| 215a | CD₃ | CD₃ | CH₃ | CH₃ | D | H | H | D |
| 216a | CD₃ | CH₃ | CD₃ | CH₃ | D | H | H | D |
| 217a | CD₃ | CH₃ | CH₃ | CD₃ | D | H | H | D |

TABLE 2-continued

Exemplary Embodiments of Formula IIa

| Compound # | R$^1$/R$^2$/R$^3$ | R$^4$ | R$^5$ | R$^6$ | Y$^{1a}$/Y$^{1b}$/Y$^{2a}$/Y$^{2b}$ | Y$^{3a}$/Y$^{3b}$/Y$^{4a}$/Y$^{4b}$/Y$^5$ | Y$^{6a}$/Y$^{6b}$/Y$^{7a}$/Y$^{7b}$/Y$^8$ | Y$^{9a}$/Y$^{9b}$/Y$^{10a}$/Y$^{10b}$/Y$^{11}$ |
|---|---|---|---|---|---|---|---|---|
| 218a | CH$_3$ | CD$_3$ | CD$_3$ | CH$_3$ | D | H | H | D |
| 219a | CH$_3$ | CD$_3$ | CH$_3$ | CD$_3$ | D | H | H | D |
| 220a | CH$_3$ | CH$_3$ | CD$_3$ | CD$_3$ | D | H | H | D |
| 221a | CD$_3$ | CD$_3$ | CD$_3$ | CH$_3$ | D | H | H | D |
| 222a | CD$_3$ | CD$_3$ | CH$_3$ | CD$_3$ | D | H | H | D |
| 223a | CD$_3$ | CH$_3$ | CD$_3$ | CD$_3$ | D | H | H | D |
| 224a | CH$_3$ | CD$_3$ | CD$_3$ | CD$_3$ | D | H | H | D |
| 225a | CD$_3$ | CD$_3$ | CD$_3$ | CD$_3$ | D | H | H | D |
| 226a | CH$_3$ | CH$_3$ | CH$_3$ | CH$_3$ | D | H | H | D |
| 227a | CD$_3$ | CH$_3$ | CH$_3$ | CH$_3$ | H | D | D | H |
| 228a | CH$_3$ | CD$_3$ | CH$_3$ | CH$_3$ | H | D | D | H |
| 229a | CH$_3$ | CH$_3$ | CD$_3$ | CH$_3$ | H | D | D | H |
| 230a | CH$_3$ | CH$_3$ | CH$_3$ | CD$_3$ | H | D | D | H |
| 231a | CD$_3$ | CD$_3$ | CH$_3$ | CH$_3$ | H | D | D | H |
| 232a | CD$_3$ | CH$_3$ | CD$_3$ | CH$_3$ | H | D | D | H |
| 233a | CD$_3$ | CH$_3$ | CH$_3$ | CD$_3$ | H | D | D | H |
| 234a | CH$_3$ | CD$_3$ | CD$_3$ | CH$_3$ | H | D | D | H |
| 235a | CH$_3$ | CD$_3$ | CH$_3$ | CD$_3$ | H | D | D | H |
| 236a | CH$_3$ | CH$_3$ | CD$_3$ | CD$_3$ | H | D | D | H |
| 237a | CD$_3$ | CD$_3$ | CD$_3$ | CH$_3$ | H | D | D | H |
| 238a | CD$_3$ | CD$_3$ | CH$_3$ | CD$_3$ | H | D | D | H |
| 239a | CD$_3$ | CH$_3$ | CD$_3$ | CD$_3$ | H | D | D | H |
| 240a | CH$_3$ | CD$_3$ | CD$_3$ | CD$_3$ | H | D | D | H |
| 241a | CD$_3$ | CD$_3$ | CD$_3$ | CD$_3$ | H | D | D | H |
| 242a | CH$_3$ | CH$_3$ | CH$_3$ | CH$_3$ | H | D | D | H |
| 243a | CD$_3$ | CH$_3$ | CH$_3$ | CH$_3$ | H | D | H | D |
| 244a | CH$_3$ | CD$_3$ | CH$_3$ | CH$_3$ | H | D | H | D |
| 245a | CH$_3$ | CH$_3$ | CD$_3$ | CH$_3$ | H | D | H | D |
| 246a | CH$_3$ | CH$_3$ | CH$_3$ | CD$_3$ | H | D | H | D |
| 247a | CD$_3$ | CD$_3$ | CH$_3$ | CH$_3$ | H | D | H | D |
| 248a | CD$_3$ | CH$_3$ | CD$_3$ | CH$_3$ | H | D | H | D |
| 249a | CD$_3$ | CH$_3$ | CH$_3$ | CD$_3$ | H | D | H | D |
| 250a | CH$_3$ | CD$_3$ | CD$_3$ | CH$_3$ | H | D | H | D |
| 251a | CH$_3$ | CD$_3$ | CH$_3$ | CD$_3$ | H | D | H | D |
| 252a | CH$_3$ | CH$_3$ | CD$_3$ | CD$_3$ | H | D | H | D |
| 253a | CD$_3$ | CD$_3$ | CD$_3$ | CH$_3$ | H | D | H | D |
| 254a | CD$_3$ | CD$_3$ | CH$_3$ | CD$_3$ | H | D | H | D |
| 255a | CD$_3$ | CH$_3$ | CD$_3$ | CD$_3$ | H | D | H | D |
| 256a | CH$_3$ | CD$_3$ | CD$_3$ | CD$_3$ | H | D | H | D |
| 257a | CD$_3$ | CD$_3$ | CD$_3$ | CD$_3$ | H | D | H | D |
| 258a | CH$_3$ | CH$_3$ | CH$_3$ | CH$_3$ | H | D | H | D |
| 259a | CD$_3$ | CH$_3$ | CH$_3$ | CH$_3$ | H | H | D | D |
| 260a | CH$_3$ | CD$_3$ | CH$_3$ | CH$_3$ | H | H | D | D |
| 261a | CH$_3$ | CH$_3$ | CD$_3$ | CH$_3$ | H | H | D | D |
| 262a | CH$_3$ | CH$_3$ | CH$_3$ | CD$_3$ | H | H | D | D |
| 263a | CD$_3$ | CD$_3$ | CH$_3$ | CH$_3$ | H | H | D | D |
| 264a | CD$_3$ | CH$_3$ | CD$_3$ | CH$_3$ | H | H | D | D |
| 265a | CD$_3$ | CH$_3$ | CH$_3$ | CD$_3$ | H | H | D | D |
| 266a | CH$_3$ | CD$_3$ | CD$_3$ | CH$_3$ | H | H | D | D |
| 267a | CH$_3$ | CD$_3$ | CH$_3$ | CD$_3$ | H | H | D | D |
| 268a | CH$_3$ | CH$_3$ | CD$_3$ | CD$_3$ | H | H | D | D |
| 269a | CD$_3$ | CD$_3$ | CD$_3$ | CH$_3$ | H | H | D | D |
| 270a | CD$_3$ | CD$_3$ | CH$_3$ | CD$_3$ | H | H | D | D |
| 271a | CD$_3$ | CH$_3$ | CD$_3$ | CD$_3$ | H | H | D | D |
| 272a | CH$_3$ | CD$_3$ | CD$_3$ | CD$_3$ | H | H | D | D |
| 273a | CD$_3$ | CD$_3$ | CD$_3$ | CD$_3$ | H | H | D | D |
| 274a | CH$_3$ | CH$_3$ | CH$_3$ | CH$_3$ | H | H | D | D |
| 275a | CD$_3$ | CH$_3$ | CH$_3$ | CH$_3$ | D | D | D | H |
| 276a | CH$_3$ | CD$_3$ | CH$_3$ | CH$_3$ | D | D | D | H |
| 277a | CH$_3$ | CH$_3$ | CD$_3$ | CH$_3$ | D | D | D | H |
| 278a | CH$_3$ | CH$_3$ | CH$_3$ | CD$_3$ | D | D | D | H |
| 279a | CD$_3$ | CD$_3$ | CH$_3$ | CH$_3$ | D | D | D | H |
| 280a | CD$_3$ | CH$_3$ | CD$_3$ | CH$_3$ | D | D | D | H |
| 281a | CD$_3$ | CH$_3$ | CH$_3$ | CD$_3$ | D | D | D | H |
| 282a | CH$_3$ | CD$_3$ | CD$_3$ | CH$_3$ | D | D | D | H |
| 283a | CH$_3$ | CD$_3$ | CH$_3$ | CD$_3$ | D | D | D | H |
| 284a | CH$_3$ | CH$_3$ | CD$_3$ | CD$_3$ | D | D | D | H |
| 285a | CD$_3$ | CD$_3$ | CD$_3$ | CH$_3$ | D | D | D | H |
| 286a | CD$_3$ | CD$_3$ | CH$_3$ | CD$_3$ | D | D | D | H |
| 287a | CD$_3$ | CH$_3$ | CD$_3$ | CD$_3$ | D | D | D | H |
| 288a | CH$_3$ | CD$_3$ | CD$_3$ | CD$_3$ | D | D | D | H |
| 289a | CD$_3$ | CD$_3$ | CD$_3$ | CD$_3$ | D | D | D | H |
| 290a | CH$_3$ | CH$_3$ | CH$_3$ | CH$_3$ | D | D | D | H |
| 291a | CD$_3$ | CH$_3$ | CH$_3$ | CH$_3$ | D | D | H | D |
| 292a | CH$_3$ | CD$_3$ | CH$_3$ | CH$_3$ | D | D | H | D |

TABLE 2-continued

Exemplary Embodiments of Formula IIa

| Compound # | R¹/R²/R³ | R⁴ | R⁵ | R⁶ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 293a | CH₃ | CH₃ | CD₃ | CH₃ | D | D | H | D |
| 294a | CH₃ | CH₃ | CH₃ | CD₃ | D | D | H | D |
| 295a | CD₃ | CH₃ | CD₃ | CH₃ | D | D | H | D |
| 296a | CD₃ | CH₃ | CH₃ | CD₃ | D | D | H | D |
| 297a | CD₃ | CH₃ | CD₃ | CD₃ | D | D | H | D |
| 298a | CH₃ | CD₃ | CD₃ | CH₃ | D | D | H | D |
| 299a | CH₃ | CD₃ | CH₃ | CD₃ | D | D | H | D |
| 300a | CH₃ | CD₃ | CD₃ | CD₃ | D | D | H | D |
| 301a | CD₃ | CD₃ | CD₃ | CH₃ | D | D | H | D |
| 302a | CD₃ | CD₃ | CH₃ | CD₃ | D | D | H | D |
| 303a | CH₃ | CD₃ | CD₃ | CD₃ | D | D | H | D |
| 304a | CH₃ | CD₃ | CD₃ | CD₃ | D | D | H | D |
| 305a | CD₃ | CD₃ | CD₃ | CD₃ | D | D | H | D |
| 306a | CH₃ | CH₃ | CH₃ | CH₃ | D | D | H | D |
| 307a | CD₃ | CH₃ | CH₃ | CH₃ | D | H | D | D |
| 308a | CH₃ | CD₃ | CH₃ | CH₃ | D | H | D | D |
| 309a | CH₃ | CH₃ | CD₃ | CH₃ | D | H | D | D |
| 310a | CH₃ | CH₃ | CH₃ | CD₃ | D | H | D | D |
| 311a | CD₃ | CD₃ | CH₃ | CH₃ | D | H | D | D |
| 312a | CD₃ | CH₃ | CD₃ | CH₃ | D | H | D | D |
| 313a | CD₃ | CH₃ | CH₃ | CD₃ | D | H | D | D |
| 314a | CH₃ | CD₃ | CD₃ | CH₃ | D | H | D | D |
| 315a | CH₃ | CD₃ | CH₃ | CD₃ | D | H | D | D |
| 316a | CH₃ | CH₃ | CD₃ | CD₃ | D | H | D | D |
| 317a | CD₃ | CD₃ | CD₃ | CH₃ | D | H | D | D |
| 318a | CD₃ | CD₃ | CH₃ | CD₃ | D | H | D | D |
| 319a | CD₃ | CH₃ | CD₃ | CD₃ | D | H | D | D |
| 320a | CH₃ | CD₃ | CD₃ | CD₃ | D | H | D | D |
| 321a | CD₃ | CD₃ | CD₃ | CD₃ | D | H | D | D |
| 322a | CH₃ | CH₃ | CH₃ | CH₃ | D | H | D | D |
| 323a | CD₃ | CH₃ | CH₃ | CH₃ | H | D | D | D |
| 324a | CH₃ | CD₃ | CH₃ | CH₃ | H | D | D | D |
| 325a | CH₃ | CH₃ | CD₃ | CH₃ | H | D | D | D |
| 326a | CH₃ | CH₃ | CH₃ | CD₃ | H | D | D | D |
| 327a | CD₃ | CD₃ | CH₃ | CH₃ | H | D | D | D |
| 328a | CD₃ | CH₃ | CD₃ | CH₃ | H | D | D | D |
| 329a | CD₃ | CH₃ | CH₃ | CD₃ | H | D | D | D |
| 330a | CH₃ | CD₃ | CD₃ | CH₃ | H | D | D | D |
| 331a | CH₃ | CD₃ | CH₃ | CD₃ | H | D | D | D |
| 332a | CH₃ | CH₃ | CD₃ | CD₃ | H | D | D | D |
| 333a | CD₃ | CD₃ | CD₃ | CH₃ | H | D | D | D |
| 334a | CD₃ | CD₃ | CH₃ | CD₃ | H | D | D | D |
| 335a | CD₃ | CH₃ | CD₃ | CD₃ | H | D | D | D |
| 336a | CH₃ | CD₃ | CD₃ | CD₃ | H | D | D | D |
| 337a | CD₃ | CD₃ | CD₃ | CD₃ | H | D | D | D |
| 338a | CH₃ | CH₃ | CH₃ | CH₃ | H | D | D | D |
| 339a | CD₃ | CH₃ | CH₃ | CH₃ | D | D | D | D |
| 340a | CH₃ | CD₃ | CH₃ | CH₃ | D | D | D | D |
| 341a | CH₃ | CH₃ | CD₃ | CH₃ | D | D | D | D |
| 342a | CH₃ | CH₃ | CH₃ | CD₃ | D | D | D | D |
| 343a | CD₃ | CD₃ | CH₃ | CH₃ | D | D | D | D |
| 344a | CD₃ | CH₃ | CD₃ | CH₃ | D | D | D | D |
| 345a | CD₃ | CH₃ | CH₃ | CD₃ | D | D | D | D |
| 346a | CH₃ | CD₃ | CD₃ | CH₃ | D | D | D | D |
| 347a | CH₃ | CD₃ | CH₃ | CD₃ | D | D | D | D |
| 348a | CH₃ | CH₃ | CD₃ | CD₃ | D | D | D | D |
| 349a | CD₃ | CD₃ | CD₃ | CH₃ | D | D | D | D |
| 350a | CD₃ | CD₃ | CH₃ | CD₃ | D | D | D | D |
| 351a | CD₃ | CH₃ | CD₃ | CD₃ | D | D | D | D |
| 352a | CH₃ | CD₃ | CD₃ | CD₃ | D | D | D | D |
| 353a | CD₃ | CD₃ | CD₃ | CD₃ | D | D | D | D |
| 354a | CH₃ | CH₃ | CH₃ | CH₃ | D | D | D | D |
| 355a | CH₃ | CH₃ | CH₃ | CH₃ | H | H | H | H | or a pharmaceutically acceptable salt thereof.

In another set of embodiments, any atom not designated as deuterium in any of the embodiments set forth above is present at its natural isotopic abundance.

In some embodiments of a compound of this invention, deuterium incorporation at each designated deuterium atom is at least 52.5%, at least 75%, at least 82.5%, at least 90%, at least 95%, is at least 97%, or at least 99%.

In some embodiments of a compound of this invention, when $Y^{1a}$ or $Y^{1b}$ is deuterium, the level of deuterium incorporation at each $Y^{1a}$ or $Y^{1b}$ is at least 52.5%, at least 75%, at least 82.5%, at least 90%, at least 95%, is at least 97%, or at least 99%.

In some embodiments of a compound of this invention, when $Y^{2a}$ or $Y^{2b}$ is deuterium, the level of deuterium incorporation at each $Y^{2a}$ or $Y^{2b}$ is at least 52.5%, at least 75%, at least 82.5%, at least 90%, at least 95%, is at least 97%, or at least 99%.

In some embodiments of a compound of this invention, when $Y^{3a}$ or $Y^{3b}$ is deuterium, the level of deuterium incorporation at each $Y^{3a}$ or $Y^{3b}$ is at least 52.5%, at least 75%, at least 82.5%, at least 90%, at least 95%, is at least 97%, or at least 99%.

In some embodiments of a compound of this invention, when $Y^{4a}$ or $Y^{4b}$ is deuterium, the level of deuterium incorporation at each $Y^{4a}$ or $Y^{4b}$ is at least 52.5%, at least 75%, at least 82.5%, at least 90%, at least 95%, is at least 97%, or at least 99%.

In some embodiments of a compound of this invention, when $Y^5$ is deuterium, the level of deuterium incorporation at each $Y^5$ is at least 52.5%, at least 75%, at least 82.5%, at least 90%, at least 95%, is at least 97%, or at least 99%.

In some embodiments of a compound of this invention, when $Y^{6a}$ or $Y^{6b}$ is deuterium, the level of deuterium incorporation at each $Y^{6a}$ or $Y^{6b}$ is at least 52.5%, at least 75%, at least 82.5%, at least 90%, at least 95%, is at least 97%, or at least 99%.

In some embodiments of a compound of this invention, when $Y^{7a}$ or $Y^{7b}$ is deuterium, the level of deuterium incorporation at each $Y^{7a}$ or $Y^{7b}$ is at least 52.5%, at least 75%, at least 82.5%, at least 90%, at least 95%, is at least 97%, or at least 99%.

In some embodiments of a compound of this invention, when $Y^8$ is deuterium, the level of deuterium incorporation at each $Y^8$ is at least 52.5%, at least 75%, at least 82.5%, at least 90%, at least 95%, is at least 97%, or at least 99%.

In some embodiments of a compound of this invention, when $Y^{9a}$ or $Y^{9b}$ is deuterium, the level of deuterium incorporation at each $Y^{9a}$ or $Y^{9b}$ is at least 52.5%, at least 75%, at least 82.5%, at least 90%, at least 95%, is at least 97%, or at least 99%.

In some embodiments of a compound of this invention, when $Y^{10a}$ or $Y^{10b}$ is deuterium, the level of deuterium incorporation at each $Y^{10a}$ or $Y^{10b}$ is at least 52.5%, at least 75%, at least 82.5%, at least 90%, at least 95%, is at least 97%, or at least 99%.

In some embodiments of a compound of this invention, when $Y^{11}$ is deuterium, the level of deuterium incorporation at each $Y^{11}$ is at least 52.5%, at least 75%, at least 82.5%, at least 90%, at least 95%, is at least 97%, or at least 99%.

In some embodiments of a compound of this invention, when $R^1$ comprises deuterium, the level of deuterium incorporation at each $R^1$ is at least 52.5%, at least 75%, at least 82.5%, at least 90%, at least 95%, is at least 97%, or at least 99%.

In some embodiments of a compound of this invention, when $R^2$ comprises deuterium, the level of deuterium incorporation at each $R^2$ is at least 52.5%, at least 75%, at least 82.5%, at least 90%, at least 95%, is at least 97%, or at least 99%.

In some embodiments of a compound of this invention, when $R^3$ comprises deuterium, the level of deuterium incorporation at each $R^3$ is at least 52.5%, at least 75%, at least 82.5%, at least 90%, at least 95%, is at least 97%, or at least 99%.

In some embodiments of a compound of this invention, when $R^4$ comprises deuterium, the level of deuterium incorporation at each $R^4$ is at least 52.5%, at least 75%, at least 82.5%, at least 90%, at least 95%, is at least 97%, or at least 99%.

In some embodiments of a compound of this invention, when $R^5$ comprises deuterium, the level of deuterium incorporation at each $R^5$ is at least 52.5%, at least 75%, at least 82.5%, at least 90%, at least 95%, is at least 97%, or at least 99%.

In some embodiments of a compound of this invention, when $R^6$ comprises deuterium, the level of deuterium incorporation at each $R^6$ is at least 52.5%, at least 75%, at least 82.5%, at least 90%, at least 95%, is at least 97%, or at least 99%.

In some embodiments of a compound of this invention, when $R^7$ comprises deuterium, the level of deuterium incorporation at each $R^7$ is at least 52.5%, at least 75%, at least 82.5%, at least 90%, at least 95%, is at least 97%, or at least 99%.

In some embodiments of a compound of this invention, when $R^8$ comprises deuterium, the level of deuterium incorporation at each $R^8$ is at least 52.5%, at least 75%, at least 82.5%, at least 90%, at least 95%, is at least 97%, or at least 99%.

The synthesis of compounds of Formula I, Ia, II and IIa may be readily achieved by synthetic chemists of ordinary skill by reference to the Exemplary Synthesis and Examples disclosed herein. Relevant procedures analogous to those of use for the preparation of compounds of Formula I, Ia, II and IIa and intermediates thereof are disclosed, for instance in Shrader, et al. Bioorganic & Medicinal Chemistry Letters 21 (2011) 3693-3698, PCT patent publications WO2013/013078, WO2013/041676, and US patent publication US2011/0172312.

Such methods can be carried out utilizing corresponding deuterated and optionally other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I and Formula Ia is depicted in Scheme 1 below.

Scheme 1: General Synthesis of Compounds of Formula I and Formula Ia

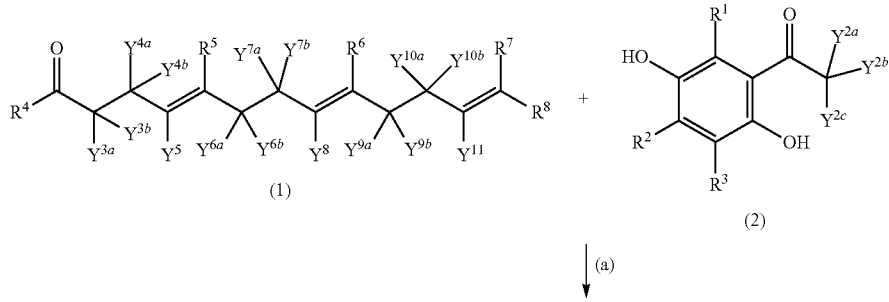

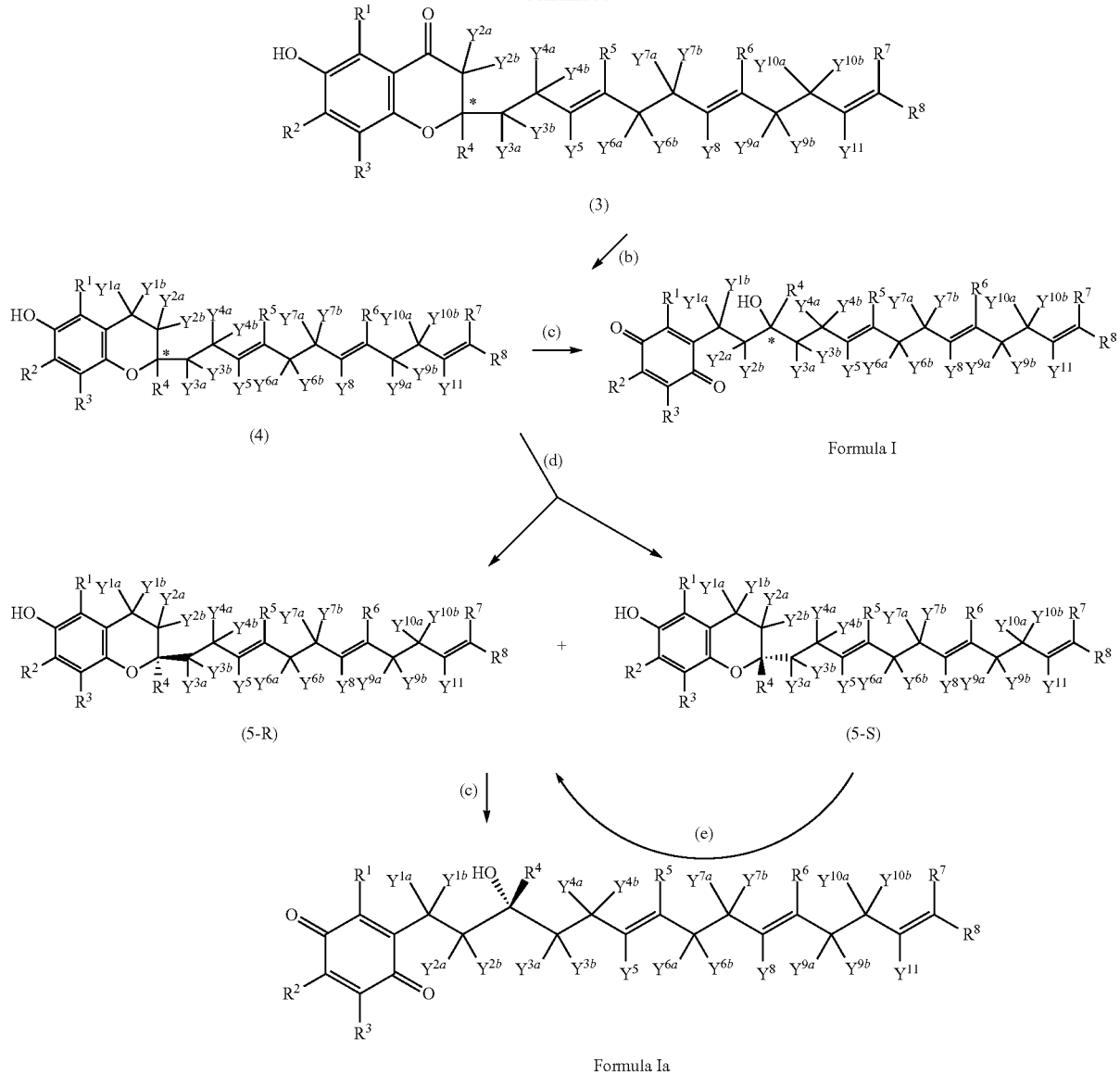

Formula Ia

Reagents and conditions: (a) Pyrrolidine; (b) Zn, HCl or DCl; (c) FeCl₃ or CAN; (d) SMB chromatography or chiral HPLC; (e) heat or NaOEt.

By analogy to a procedure described by Kabbe, H. et al., Synthesis 1978; 1978(12): 888-889, and described in WO2013041676, appropriately deuterated farnesylacetone intermediate (I) is condensed with appropriately deuterated dihydroxy acetophenone (2) in the presence of a base such as pyrrolidine, producing a racemic mixture of appropriately deuterated 4-oxo-α-tocotrienol intermediate (3). Selective single-stage reduction of the keto moiety of intermediate (3) with metallic zinc in HCl or DCl, produces a racemic mixture of appropriately and correspondingly deuterated α-tocotrienol intermediate (4) in a manner analogous to a procedure described in U.S. Pat. No. 6,096,907. Finally, treatment of (4) with oxidizing reagent such as ferric (III) chloride hexahydrate produces a racemic mixture of appropriately deuterated α-tocotrienol quinone compounds of Formula I. Alternatively, treatment with cerium (IV) ammonium nitrate at low temperature affords a racemic mixture of appropriately deuterated α-tocotrienol quinone compounds of Formula I by analogy to a procedure described by He, L. et al., Eur. J. Org. Chem. 2008, 1869.

When the racemic mixture of intermediate (4) is chromatographically separated by means of simulated moving bed (SMB) chromatography or chiral HPLC appropriately deuterated R-α-tocotrienol (5-R) and S-α-tocotrienol (5-S) intermediates are produced. Isomerization of S-α-tocotrienol intermediate (5-S) under thermal conditions, or by contacting with a base such as sodium ethoxide, furnishes the corresponding and appropriately deuterated R-α-tocotrienol intermediate (5-R). Finally, treatment of intermediate (5-R) with oxidizing reagent such as ferric (III) chloride hexahydrate or cerium (IV) ammonium nitrate produces appropriately deuterated R-α-tocotrienol quinone compounds of Formula Ia.

Furthermore, the synthesis of compounds of Formula II and Formula IIa, may be readily achieved by synthetic chemists of ordinary skill by reference to the exemplary synthesis depicted in Scheme 2. Relevant procedures analogous to those of use for the preparation of compounds of Formula II and Formula IIa and intermediates thereof are disclosed using well known methods in the art disclosed, for instance in WO2013013078 and CH 356754. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

A convenient method for synthesizing compounds of Formula II and Formula IIa is depicted in Scheme 2 below.

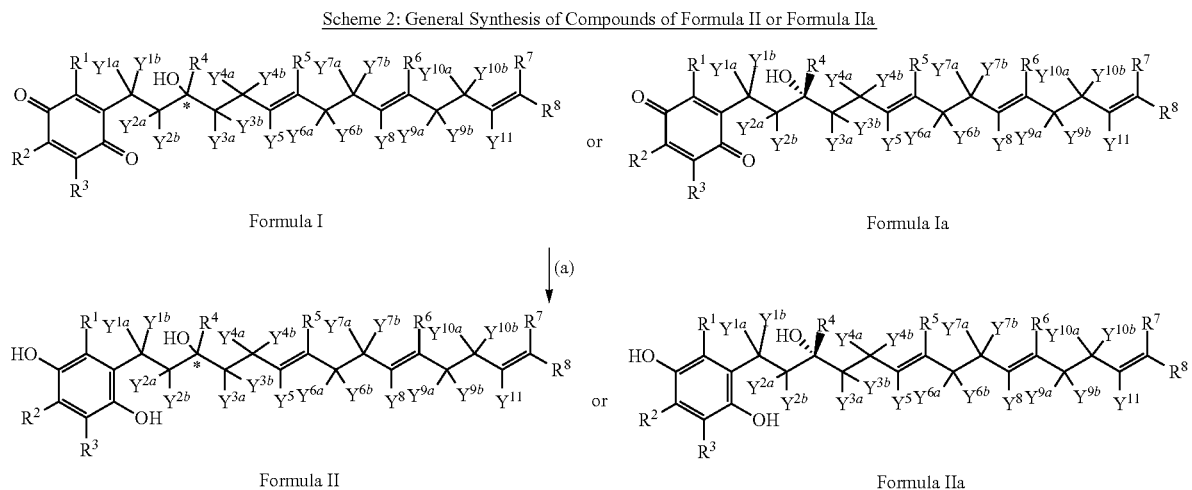

Reagents and condtions:
(a) Na$_2$S$_2$O$_4$

In a manner analogous to a procedure described in CH 356754, a racemic mixture of appropriately deuterated α-tocotrienol quinone of Formula I, or appropriately deuterated R-α-tocotrienol quinone of Formula Ia is treated with a suitable reducing agent such as sodium dithionite to produce a racemic mixture of appropriately deuterated α-tocotrienol hydroquinone of Formula II or appropriately deuterated R-α-tocotrienol quinone of Formula IIa.

Using commercially available reagents and deuterated reagents that can be readily prepared by known methods, compounds of Formula I, Formula Ia, Formula II and Formula IIa can be prepared with greater than 90% or greater than 95% deuterium incorporation at each position designated as D (see below for details).

Appropriately deuterated intermediate (1), for use in the preparation of compounds of Formula I and Formula Ia according to Scheme 1 may be prepared from corresponding deuterated reagents exemplified in Scheme 3 below.

Scheme 3: Preparation of Intermediate (1)

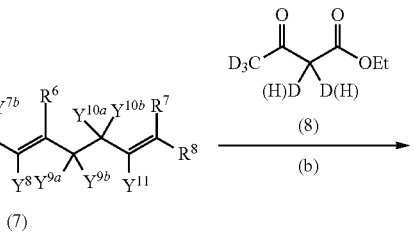

Reagents and conditions: (a) PBr$_3$ or PPh$_3$, CBr$_4$; (b) NaOEt; (c) 5N KOH, H$_2$O or D$_2$O In a manner analogous to a procedure delineated in WO2014151719, appropriately deuterated farnesol intermediate (6) is treated with a bromonium ion source such as phosphorus tribromide to furnish appropriately deuterated farnesyl bromide intermediate (7), which is subsequently treated with appropriately deuterated acetoacetate intermediate (8) in the presence of a base such as sodium ethoxide, producing appropriately deuterated farnesyl β-keto ester intermediate (9). Decarboxylation of homologated keto ester (9) using 5N KOH in D$_2$O or H$_2$O furnishes appropriately and correspondingly deuterated farnesyl acetone intermediate (1).

Butanoic-2,2,4,4,4-$d_5$ acid, 3-oxo-, ethyl ester (8a) is prepared as described by Citron, C. et al., Eur. J. Org. Chem., 2014: 7684-7691.

Use of appropriately deuterated reagents allows deuterium incorporation at the $Y^{3a,3b}$, $Y^{4a, 4b}$, $Y^5$, $Y^{6a, 6b}$, $Y^{7a, 7b}$, $Y^8$, $Y^{9a, 9b}$, $Y^{10a, 10b}$, $Y^{11}$, $R^4$, $R^5$, $R^6$, $R^7$, $R^8$ positions of a compound of Formula I, Ia, II and IIa or any appropriate intermediate herein, e.g., 90, 95, 97, or 99%; deuterium incorporation at any $Y^{3a,3b}$, $Y^{4a, 4b}$, $Y^5$, $Y^{6a, 6b}$, $Y^{7a, 7b}$, $Y^8$, $Y^{9a, 9b}$, $Y^{10a, 10b}$, $Y^{11}$, and/or $R^4$, $R^5$, $R^6$, $R^7$, $R^8$.

Using commercially available reagents and deuterated reagents that can be readily prepared by known methods, compounds of Formula I, Ia, II and IIa can be prepared with greater than 90% or greater than 95% deuterium incorporation at each position designated as D (see below for details).

Appropriately deuterated intermediate (2), for use in the preparation of compounds of Formula I and Formula Ia according to Scheme 1 may be prepared from corresponding deuterated reagents exemplified in Scheme 4 below.

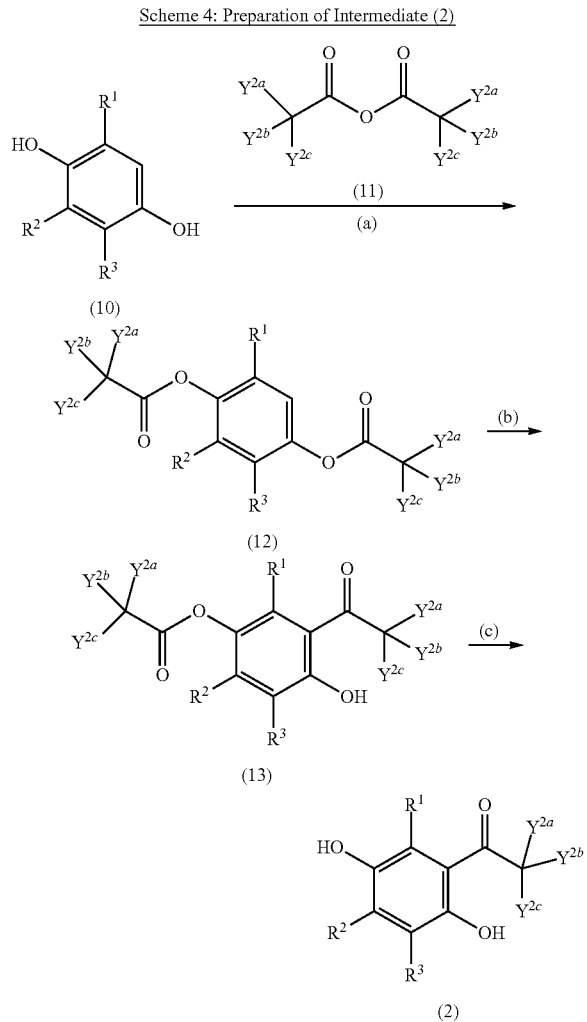

Reagents and conditions:
(a) EtN(Pr-i)$_2$;
(b) BF$_3$/AcOH;
(c) NaOH or NaOMe

In a manner analogous to a procedure described in US 20060128790, appropriately deuterated hydroquinone (10) is acylated with appropriately deuterated anhydride (11) in the presence of Hunig's base to furnish appropriately deuterated bis-acetylated quinone (12). Subsequent Fries rearrangement reaction catalyzed by BF$_3$ in acetic acid produces appropriately deuterated mono-acetylated quinone (13). Finally, base hydrolysis of (13) using sodium hydroxide or sodium methoxide produces appropriately deuterated dihydroxy acetophenone intermediate (2) by analogy to a procedure described by Manecke, G. et al., Chem. Ber., 95, 1413 (1962) or Cohen, N. et al., Journal of Organic Chemistry, 43(19), 3723-6; 1978.

Acetic anhydride-$d_6$ (99 atom % D) (11a) is commercially available.

Use of appropriately deuterated reagents allows deuterium incorporation at the $Y^{2a, 2b, 2c}$, $R^1$, $R^2$, $R^3$ positions of a compound of Formula I, Ia, II and IIa or any appropriate intermediate herein, e.g., 90, 95, 97, or 99% deuterium incorporation at any $Y^{2a, 2b, 2c}$, $R^1$, $R^2$, and/or $R^3$.

Using commercially available reagents and deuterated reagents that can be readily prepared by known methods, compounds of Formula I, Ia, II and IIa can be prepared with greater than 90% or greater than 95% deuterium incorporation at each position designated as D (see below for details).

Appropriately deuterated intermediate (6), for use in the preparation of compounds of Formula I and Ia according to Scheme 1 may be prepared from corresponding deuterated reagents exemplified in Scheme 5 below.

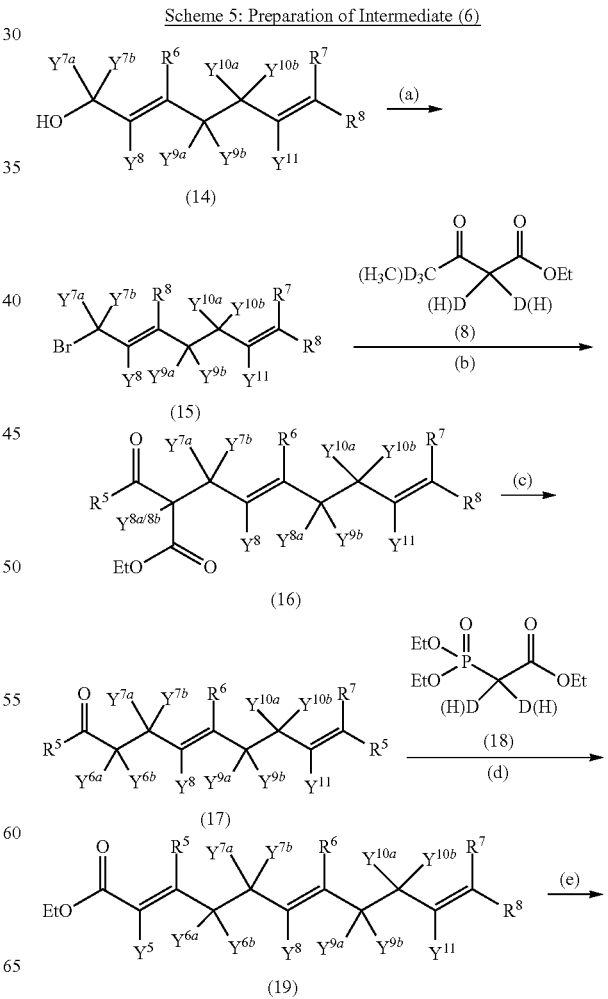

-continued

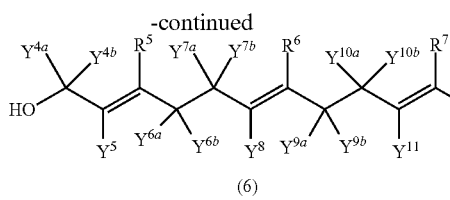

(6)

Reagents and conditions:
(a) PBr$_3$ or PPh$_3$, CBr$_4$,
(b) NaOEt or K$_2$CO$_3$;
(c) 5N KOH/H$_2$O or 5N KOD/D$_2$O;
(d) NaH;
(e); LAD or LAH In a manner analogous to a procedure described by Hoshino, T. et al., Journal of Labelled Compounds and Radiopharmaceuticals, 28(11), 1285-92; 1990, appropriately deuterated geranyl bromide intermediate (15) derived from appropriately deuterated geraniol (14) following treatment with PBr$_3$ by analogy to a procedure described in WO2014151719, is treated with deuterated acetoacetate intermediate (8) in the presence of a base such as sodium ethoxide, producing appropriately deuterated geranyl β-keto ester intermediate (16). Decarboxylation of the keto ester (16) using 5N KOH in D20 or H$_2$O furnishes appropriately and correspondingly deuterated geranyl acetone intermediate (17). Subsequent Horner-Wadsworth-Emmons olefination with appropriately deuterated phosphonoacetate intermediate (18) in the presence of NaH produces appropriately deuterated farnesyl ethyl ester intermediate (19). Finally, reduction with LiAlH$_4$ or LiAlD$_4$ produces appropriately and correspondingly deuterated farnesol intermediate (6).

Butanoic-2,2,4,4,4-d$_5$ acid, 3-oxo-, ethyl ester (8a), and triethyl phosphonoacetate-d$_2$ (18a) may be prepared in accordance with a procedure described by Citron, C. et al., Eur. J. Org. Chem., 2014: 7684-7691.

Use of appropriately deuterated reagents allows deuterium incorporation at the $Y^{4a, 4b}$, $Y^5$, $Y^{6a, 6b}$, $Y^{7a, 7b}$, $Y^8$, $Y^{9a, 9b}$, $Y^{10a, 10b}$, $Y^{11}$, $R^5$, $R^6$, $R^7$, $R^8$ positions of a compound of Formula I, Formula Ia, Formula II and Formula IIa or any appropriate intermediate herein, e.g., 90, 95, 97, or 99% deuterium incorporation at any $Y^{4a, 4b}$, $Y^5$, $Y^{6a, 6b}$, $Y^{7a, 7b}$, $Y^8$, $Y^{9a, 9b}$, $Y^{10a, 10b}$, $Y^{11}$, and/or $R^5$, $R^6$, $R^7$, $R^8$.

Using commercially available reagents and deuterated reagents that can be readily prepared by known methods, compounds of Formula I, Formula Ia, Formula II and Formula IIa can be prepared with greater than 90% or greater than 95% deuterium incorporation at each position designated as D (see below for details).

Appropriately deuterated intermediate (10), for use in the preparation of compounds of Formula I and Formula Ia according to Scheme 1 may be prepared from corresponding deuterated reagents exemplified in Scheme 6 below.

Scheme 6: Prepration of Intermediate (10)

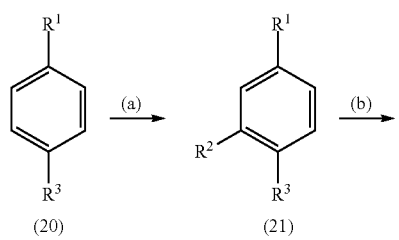

-continued

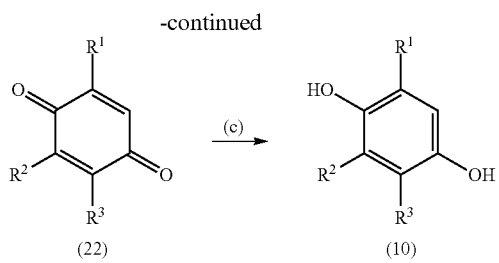

Reagents and conditions:
(a) methanol-d$_4$ (99.8 atom % D) or methanol, Al$_2$O$_3$, SiO$_2$;
(b) H$_2$O$_2$, 2,4-dichloro-6-phenyliminomethyl-phenol, MTO;
(c) Ammonium formate, Pd-C In a manner analogous to a procedure described by Raj, A. et al., Journal of Catalysis, 138(2), 518-24; 1992, or as described in CN 101654394, appropriately deuterated p-xylene intermediate (20) is alkylated with methanol-d$_4$ (99.8 atom % D) or methanol in the presence of acidic catalyst such as metallosilicate molecular sieves to furnish appropriately and correspondingly deuterated trimethylbenzene intermediate (21). Subsequent ligand assisted methyltrioxorhenium catalyzed oxidation using hydrogen peroxide, in the presence of a Lewis base such as 2,4-dichloro-6-phenyliminomethyl-phenol, as ligand furnishes appropriately deuterated benzoquinone intermediate (22) by analogy to a procedure described by Carril, M. et al., Journal of Catalysis, 283(1), 55-67; 2011. Finally, catalytic transfer hydrogenation produces appropriately deuterated dihydroquinone intermediate (10) by analogy to a procedure described by Pande, P. et al., Asian Journal of Chemistry, 22(4), 2549-2553; 2010.

The following intermediates are commercially available: p-Xylene-(dimethyl-d$_6$) (99 atom % D) (20a), p-Xylene-α, α,α-d$_3$ (99 atom % D) (20b).

Use of appropriately deuterated reagents allows deuterium incorporation at the $R^1$, $R^2$, $R^3$ positions of a compound of Formula I, Formula Ia, Formula II and Formula IIa or any appropriate intermediate herein, e.g., 90, 95, 97, or 99% deuterium incorporation at any $R^1$, $R^2$, and/or $R^3$.

Using commercially available reagents and deuterated reagents that can be readily prepared by known methods, compounds of Formula I, Formula Ia, Formula II and Formula IIa can be prepared with greater than 90% or greater than 95% deuterium incorporation at each position designated as D (see below for details).

Appropriately deuterated intermediate (14), for use in the preparation of compounds of Formula I and Formula Ia according to Scheme 1 may be prepared from corresponding deuterated reagents exemplified in Scheme 7 below.

Scheme 7: Preparation of Intermediate (14)

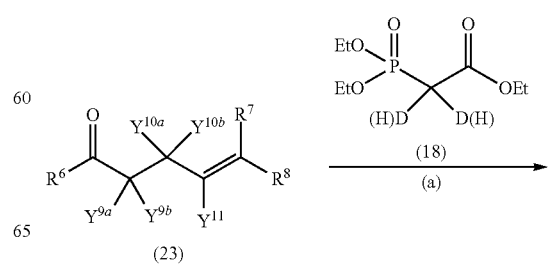

-continued

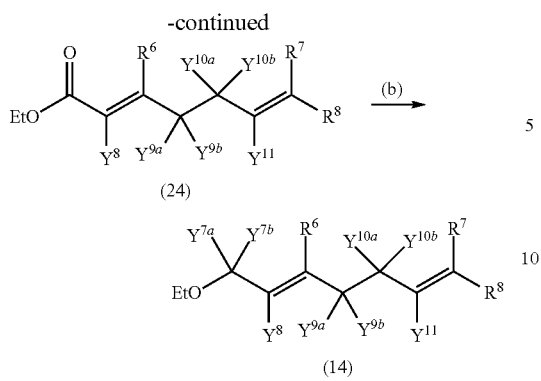

(24)

(14)

Reagents and conditions:
(a) BuLi;
(b) Dibal-H or Dibal-D (98 atom % D)

In a manner analogous to a procedure described by van der Klei, A. et al., Eur. J. Org. Chem. 2002, 3015-3023, appropriately deuterated heptenone intermediate (23) is treated with appropriately deuterated phosphonoacetate intermediate (18) in a Wittig reaction using n-butyl lithium to produce appropriately deuterated diene ethyl ester intermediate (24), which is subsequently treated with reducing agent such as Dibal-H or Dibal-D to furnish appropriately and correspondingly deuterated geraniol (14).

Triethyl phosphonoacetate-$d_2$ (18a) may be prepared according to a procedure described by Citron, C. et al., Eur. J. Org. Chem., 2014: 7684-7691.

Use of appropriately deuterated reagents allows deuterium incorporation at the $Y^{7a, 7b}$, $Y^8$, $Y^{9a, 9b}$, $Y^{10a, 10b}$, $Y^{11}$, $R^6$, $R^7$, $R^8$ positions of a compound of Formula I, Formula Ia, Formula II and Formula IIa or any appropriate intermediate herein, e.g., 90, 95, 97, or 99% deuterium incorporation at any $Y^{7a, 7b}$, $Y^8$, $Y^{9a, 9b}$, $Y^{10a, 10b}$, $Y^{11}$, and/or $R^6$, $R^7$, $R^8$.

Using commercially available reagents and deuterated reagents that can be readily prepared by known methods, compounds of Formula I, Formula Ia, Formula II and Formula IIa can be prepared with greater than 90% or greater than 95% deuterium incorporation at each position designated as D (see below for details).

Appropriately deuterated intermediate (23), for use in the preparation of compounds of Formula I and Formula Ia according to Scheme 1 may be prepared from corresponding deuterated reagents exemplified in Scheme 8 below.

Scheme 8: Preparation of Intermediate (23)

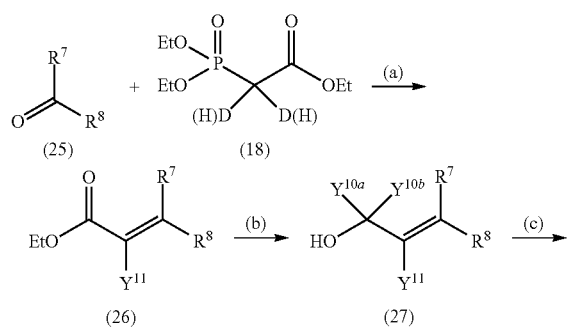

-continued

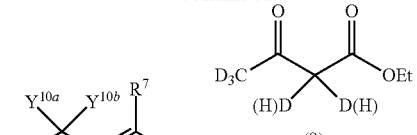

(28)

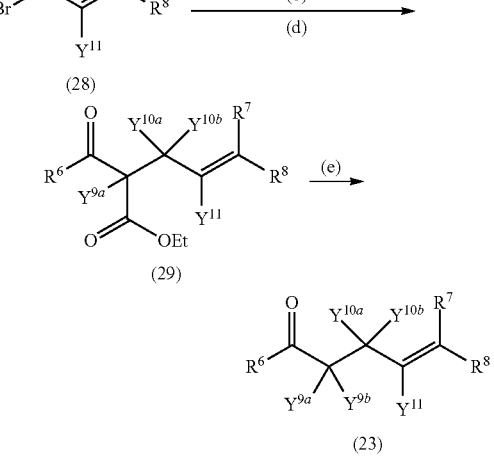

(29)

(23)

Reagents and conditions:
(a) LDA;
(b) LiAlH$_4$ or LiAlD$_4$;
(c) PBr$_3$;
(d) K$_2$CO$_3$;
(e) KOD, D$_2$O, EtOD, DCl or KOH, H$_2$O, EtOH, HCl In a manner analogous to a procedure described by Citron C. et al., Eur. J. Org. Chem. 2014, 7684-7691, Horner-Wadsworth-Emmons olefination of appropriately deuterated acetone intermediate (25) with phosphonoacetate (18) affords appropriately deuterated acrylate intermediate (26), which is subsequently reduced with LAH or LAD to furnish appropriately and correspondingly deuterated prenol intermediate (27). Treatment of (27) with a bromonium ion source such as phosphorus tribromide affords appropriately deuterated prenyl bromide intermediate (28), which is subsequently alkylated with appropriately deuterated acetoacetate intermediate (8) to produce β-keto ester intermediate (29). Finally, decarboxylation using KOD in D$_2$O/EtOD or KOH in H$_2$O/EtOH, followed by acidic work up with DCl, or HCl, furnishes appropriately and correspondingly deuterated heptenone intermediate (23).

Butanoic-2,2,4,4,4-$d_5$ acid, 3-oxo-, ethyl ester (8a) is prepared as described by Citron, C. et al., Eur. J. Org. Chem., 2014: 7684-7691. The following intermediates are commercially available: Acetone-$d_6$ (99.9 atom % D) (25a), Acetone-1,1,1-$d_3$ (98 atom % D) (25b). Triethyl phosphonoacetate-d2 (18a) may be prepared in accordance with a procedure described by Citron, C. et al., Eur. J. Org. Chem., 2014: 7684-7691.

Use of appropriately deuterated reagents allows deuterium incorporation at the $Y^{9a, 9b}$, $Y^{10a, 10b}$, $Y^{11}$, $R^6$, $R^7$, $R^8$ positions of a compound of Formula I, Formula Ia, Formula II and Formula IIa or any appropriate intermediate herein, e.g., 90, 95, 97, or 99% deuterium incorporation at any $Y^{9a, 9b}$, $Y^{10a, 10b}$, $Y^{11}$, and/or $R^6$, $R^7$, $R^8$.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I or Ia and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, $3^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I, Ia, II and IIa, or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562, 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to be useful in the treatment of one or more of the following disease or conditions: Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, Multisystem genetic disorders, Tourette's disease, metabolic disorders, other mitochondrial disorders, Leber's hereditary optic neuropathy, and Huntington's disease.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 10-2,000 mg/day, from 50-1200 mg/day, from 100-1200 mg/day, from 50-300 mg/day, and from 300-1200 mg/day. Dosing of the compound of this invention can be once, twice, three times or four time per day to achieve the daily dose. In other embodiments, an effective amount of a compound of this invention can range from 1-15 mg/kg body weight, from 5-15 mg/kg body weight, and from 1-5 mg/kg body weight, where dosing of this amount occurs once, twice, three times or four time per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of treating a disease or condition selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, Multisystem genetic disorders, Tourette's disease, metabolic disorders, mitochondrial disorders, Leber's hereditary optic neuropathy, and Huntington's disease in a subject in need thereof, comprising the step of administering to the subject an effective amount of a compound or a composition of this invention. In one embodiment the subject is a patient in need of such treatment.

In one particular embodiment, the method of this invention is used to treat a disease or condition selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, Multisystem genetic disorders, Tourette's disease, and Leber's hereditary optic neuropathy in a subject in need thereof.

In another particular embodiment, the method of this invention is used to treat Leigh syndrome in a subject in need thereof.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful in the treatment of one or more of Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, Multisystem genetic disorders, Tourette's disease, metabolic disorders, mitochondrial disorders, Leber's hereditary optic neuropathy, or Huntington's disease. The choice of second therapeutic agent is also dependent upon the particular disease or condition to be treated.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I, Ia, II or IIa alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula I, Ia, II or IIa for use in the treatment in a subject of a disease, disorder or symptom thereof delineated herein.

EXAMPLES

Example 1. Synthesis of Compound 355

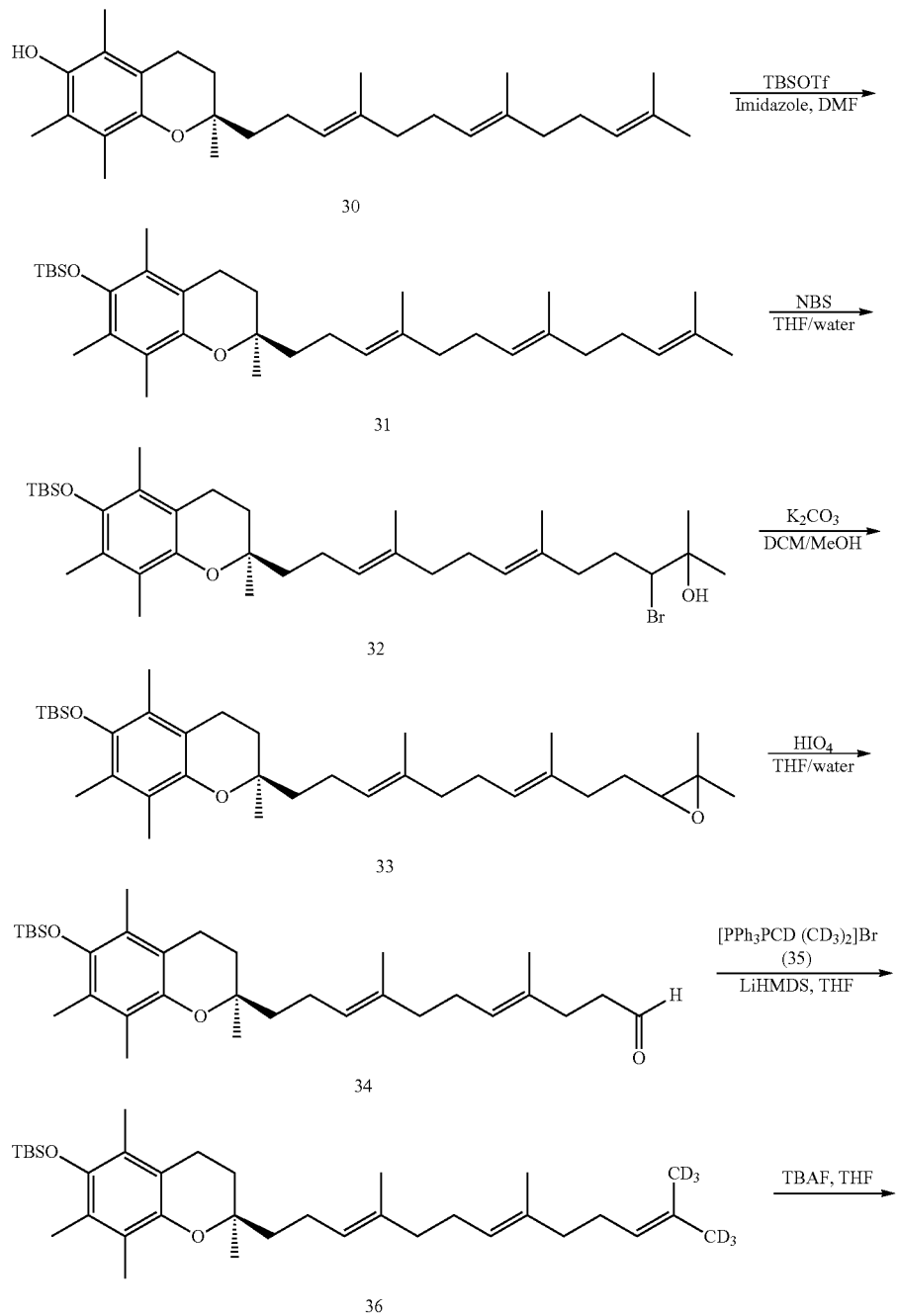

Scheme 9: Preparation of Compound 355

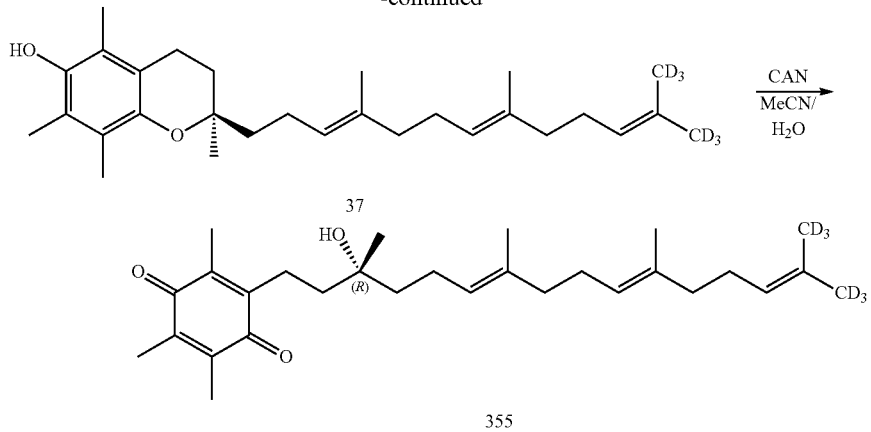

tert-Butyldimethyl(((R)-2,5,7,8-tetramethyl-2-((3E,7E)-4,8,12-trimethyltrideca-3,7,11-trien-1-yl)chroman-6-yl)oxy)silane (31)—tertButyldimethylsilyl trifluoromethanesulfonate (TBSOTf) (4.06 mL, 17.7 mmol, 1.5 equiv) was added at room temperature to a solution of D-α-tocotrienol (30, BocSci, Lot #B16Q101101) (5.00 g, 11.8 mmol, 1 equiv) and imidazole (3.21 g, 47.2 mmol, 4 equiv) in DMF (20 mL). The reaction mixture was heated at 85° C. for 16 hours, diluted with water (200 mL), and extracted with MTBE (3×200 mL). The combined organic layer was washed with brine (200 mL), dried over sodium sulfate, filtered and concentrated under reduced pressure. The residue was purified using an AnaLogix automated chromatography system (Gold column 80 g), eluting with 0-60% dichloromethane in heptanes to give 31 (6.63 g, quantitative yield) as a white cloudy oil.

(6E,10E)-3-Bromo-13-((R)-6-((tert-butyldimethylsilyl)oxy)-2,5,7,8-tetramethylchroman-2-yl)-2,6,10-trimethyltrideca-6,10-dien-2-ol (32)—N-Bromosuccinimide (NBS) (2.10 g, 11.8 mmol, 1 equiv) was added in portions at 0° C. to a solution of 31 (6.63 g, 11.8 mmol, 1 equiv) in THF (120 mL) and water (17 mL). The reaction mixture was stirred at room temperature for 16 hours, was again cooled to 0° C. and additional N-bromosuccinimide (0.21 g, 1.18 mmol, 0.1 equiv) was added. The reaction mixture was stirred at room temperature for 3 hours, was again cooled to 0° C. and additional N-bromosuccinimide (0.21 g, 1.18 mmol, 0.1 equiv) was added. The reaction mixture was stirred at room temperature for 2 hours, diluted with water (200 mL), and extracted with MTBE (3×200 mL). The combined organic layer was dried over sodium sulfate, filtered, and concentrated under reduced pressure. The residue was purified using an AnaLogix automated chromatography system (Gold column, 80 g), eluting with 0-100% dichloromethane in heptanes to give 32 (6.2 g, 83% yield) as a beige oil.

tert-Butyl(((2R)-2-((3E,7E)-10-(3,3-dimethyloxiran-2-yl)-4,8-dimethyldeca-3,7-dien-1-yl)-2,5,7,8-tetramethylchroman-6-yl)oxy)dimethylsilane (33)—A saturated solution of potassium carbonate in methanol (120 mL) was added at room temperature to a solution of 32 (6.2 g, 9.76 mmol, 1 equiv) in dichloromethane (17 mL). The reaction was allowed to stir at room temperature for 16 hours, concentrated, and dichloromethane (200 mL) was added. The mixture was filtered, concentrated under reduced pressure, and purified using an AnaLogix automated chromatography system, eluting with 0-60% dichloromethane in heptanes to give 33 (3.3 g, 61% yield) as a beige oil.

(4E,8E)-11-((R)-6-((tert-Butyldimethylsilyl)oxy)-2,5,7,8-tetramethylchroman-2-yl)-4,8-dimethylundeca-4,8-dienal (34)—Periodic acid (0.23 g, 0.99 mmol, 1.1 equiv) was added in one portion at 0° C. to a solution of 33 (0.50 g, 0.90 mmol, 1 equiv) in THF (10 mL) and water (10 mL). The reaction mixture was stirred at 0° C. for 2 hours and then room temperature for 16 hours. The mixture was partitioned between water (10 mL) and ethyl acetate (10 mL). The layers were separated and the organic layer was dried over sodium sulfate, filtered, and concentrated under reduced pressure. The residue was purified using an AnaLogix automated chromatography system, eluting with 0-60% dichloromethane in heptanes to give 34 (0.40 g, 87% yield) as a clear oil.

Triphenyl-(1,2,2,2-d4-1-methyl-d3-ethyl)phosphonium bromide (35)—2-Bromo-(1,1,1,2,3,3,3-d7)-propane (99.8%-d7, CDN, Lot #I-458) (10.0 g, 76.9 mmol, 1 equiv) and triphenylphosphine (21.2 g, 80.8 mmol, 1.05 equiv) were heated at 150° C. in a sealed tube for 2 days, cooled and recrystallized from hot ethanol (10 mL) and ethyl acetate (200 mL). The solid was filtered, washed with ethyl acetate and dried in vacuum oven at 40° C. for 1 hour to give 35 (4.75 g, 16% yield) as a white solid.

tert-Butyl(((R)-2-((3E,7E)-4,8-dimethyl-12-(methyl-d3)trideca-3,7,11-trien-1-yl-13,13,13-d3)-2,5,7,8-tetramethylchroman-6-yl)oxy)dimethylsilane (36)—Anhydrous THF (4 mL) was added at room temperature to a mixture of potassium tert-butoxide (0.051 g, 0.46 mmol, 1.8 equiv) and 35 (0.20 g, 0.51 mmol, 2 equiv) resulting in the formation of a dark red color. The reaction mixture was stirred at room temperature for 5 minutes followed by the addition of a solution of 34 (0.13 g, 0.26 mmol, 1 equiv) in anhydrous THF (2 mL). The reaction mixture was stirred at room temperature for 16 hours. Additional anhydrous THF (4 mL) was added at room temperature to a mixture of potassium tert-butoxide (0.051 g, 0.46 mmol, 1.8 equiv) and 35 (0.20 g, 0.51 mmol, 2 equiv). The resulting dark red mixture was added to the above reaction within 5 minutes. The reaction mixture was stirred at room temperature for 16 hours. Additional anhydrous THF (4 mL) was added at room temperature to a mixture of potassium tert-butoxide (0.051 g, 0.46 mmol, 1.8 equiv) and 35 (0.20 g, 0.51 mmol, 2 equiv). The resulting dark red mixture was added to the above reaction within 3 minutes. The reaction mixture was stirred at room temperature for 16 hours. The reaction mixture was quenched with saturated aqueous ammonium chloride (10 mL) and extracted with ethyl acetate (3×10 mL). The combined organic layer was washed with brine, dried over sodium sulfate, filtered, and concentrated under reduced pressure. The residue was purified using an AnaLogix automated chromatography system, eluting with 0-40% dichloromethane in heptanes to give 36 (0.10 g, 73% yield, contains ~30% PPh3) as a clear oil.

(R)-2-((3E,7E)-4,8-Dimethyl-12-(methyl-d3)trideca-3,7,11-trien-1-yl-13,13,13-d3)-2,5,7,8-tetramethylchroman-6-ol (37)—Tetrabutylammonium fluoride (TBAF) solution (1.0 M in THF, 0.92 mL, 0.92 mmol, 5 equiv) was added dropwise at room temperature to a solution of 36 (0.10 g, 0.18 mmol, 1 equiv) in THF (4 mL). The reaction mixture was stirred at room temperature for 2 hours, concentrated under reduced pressure, and purified using an AnaLogix automated chromatography system, eluting with 0-50% dichloromethane in heptanes to give 37 (28 mg, 51% yield) as a beige oil.

2-((R,6E,10E)-3-Hydroxy-3,7,11-trimethyl-15-(methyl-d3)hexadeca-6,10,14-trien-1-yl-16,16,16-d3)-3,5,6-trimethylcyclohexa-2,5-diene-1,4-dione (Compound 355)—A solution of cerium (IV) ammonium nitrate (0.03 g, 0.056 mmol, 3 equiv) in water (0.8 mL) was added at room temperature to a solution of 37 (0.008 g, 0.019 mmol, 1 equiv) in acetonitrile (0.6 mL). The reaction mixture was stirred at room temperature for 30 minutes, extracted with dichloromethane (3×2 mL), dried over sodium sulfate, filtered and concentrated under reduced pressure. The residue was purified using an AnaLogix automated chromatography system (Gold column, 4 g), eluting with 0-20% ethyl acetate in heptanes to give Compound 355 (2 mg, 25% yield) as a yellow oil. $^1$H-NMR (CDCl$_3$, 400 MHz): δ 1.26 (m, 4H), 1.53 (m, 4H), 1.57 (m, 2H), 1.60 (s, 3H), 1.64 (s, 3H), 1.96 (m, 3H), 2.01 (m, 7H), 2.05 (s, 3H), 2.09 (m, 4H), 2.55 (m, 2H), 5.10 (m, 3H); MS (ESI): 447.3 [(M+H)$^+$].

Example 2. Synthesis of Compound 100

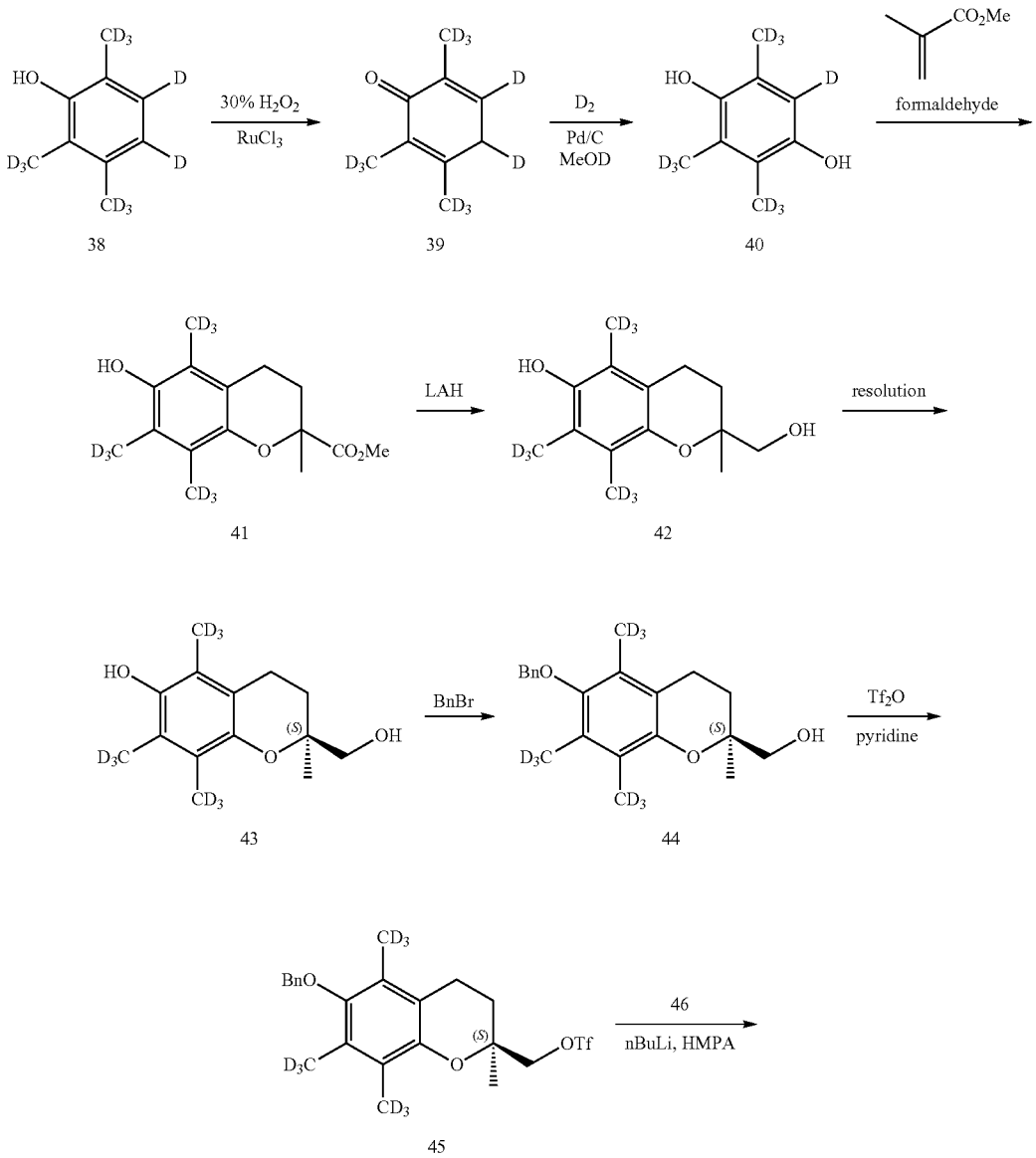

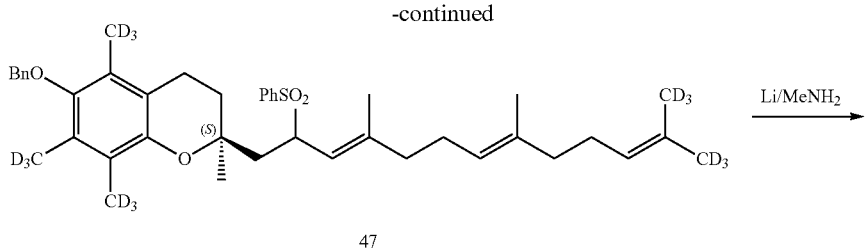

47

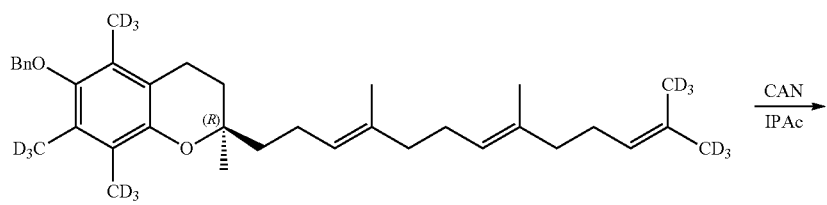

48

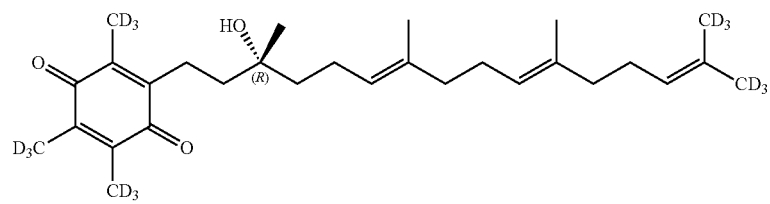

100

2,3,5-Tris(methyl-d3)cyclohexa-2,5-diene-1,4-dione-6-d (39)—To a solution of 38 (1.5 g, 10.2 mmol, 1 equiv, available from CDN isotopes, 99 atom % D) and ruthenium trichloride (23 mg, 0.10 mmol, 0.01 equiv) in acetic acid (15 mL) was added hydrogen peroxide (2.3 mL of a 30% aqueous solution, 20.4 mmol, 2 equiv) drop-wise. The reaction mixture was stirred at room temperature for 5 hours. The reaction was quenched by the addition of 10% aqueous sodium thiosulfate (20 mL). The mixture was extracted with diethyl ether (5×25 mL). The combined organic layer was dried over sodium sulfate, filtered, and concentrated under reduced pressure. The crude material was purified using an Analogix automated chromatography system eluting with 25% ethyl acetate in heptanes yielding 39 (670 mg, 41% yield).

2,3,5-Tris(methyl-d3)benzene-6-d-1,4-diol (40)—A 500-mL Parr shaker bottle was charged with 39 (300 mg), 10% Pd/C (150 mg, dry) and methanol-OD (20 mL). The reaction was hydrogenated at 40 psi deuterium for 2 days. The reaction mixture was filtered through a pad of Celite and the filtrate was concentrated under reduced pressure to yield 40 (220 mg, 73% yield) which was used as such.

Methyl 6-hydroxy-2-methyl-5,7,8-tris(methyl-d3)chromane-2-carboxylate (41)—A 10 mL microwave vial was charged with 40 (100 mg, 0.62 mmol, 1 equiv), formaldehyde (46 mg of a 37% solution in water with 10-15% methanol), and methyl methacrylate (0.31 mg, 3.1 mmol, 5 equiv). The vial was sealed and heated at 160° C. for 3 hours to yield 41; MS (ESI): 274.2 [(M+H)⁺].

Compound 100 is synthesized from intermediate 41 according to the literature procedures in *Bioorganic and Medicinal Chemistry Letters*, 2011, p. 3693-3698; *Bioorganic and Medicinal Chemistry*, 2006, p. 5389-5396; and *European Journal of Organic Chemistry*, 2014, p. 7684-7691; all of which are incorporated by reference in their entirety. Intermediate 46, for use in the synthesis of Compound 100, is prepared as described below.

Scheme 11: Preparation of Intermediate 46

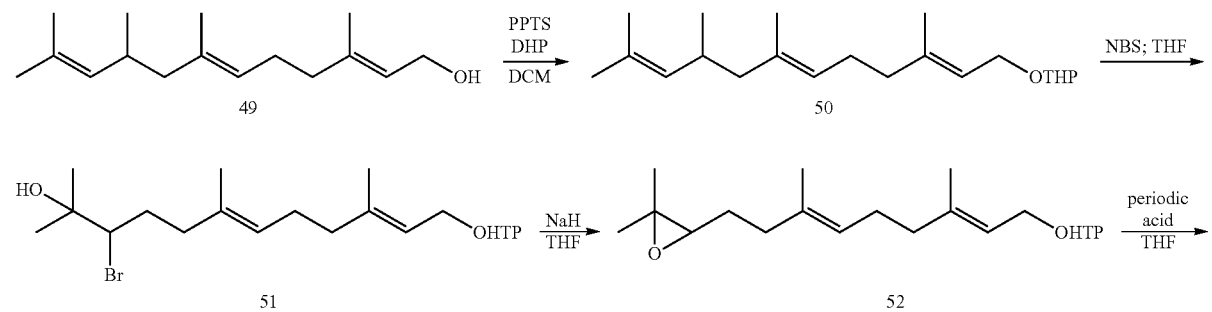

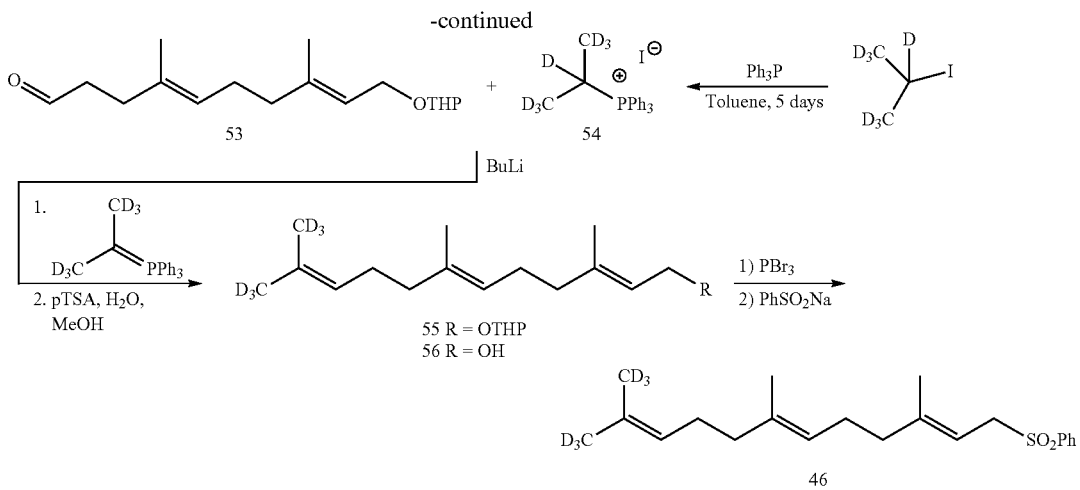

2-(((2E,6E)-3,7,11-Trimethyldodeca-2,6,10-trien-1-yl)oxy)tetrahydro-2H-pyran (50)—Pyridinium p-toluenesulfonate (1.2 g, 11.3 mmol, 0.25 equiv) was added to a solution of 49 (5.0 g, 22.5 mmol, 1 equiv) and 3,4-dihydro-2H-pyran (2.35 g, 28 mmol, 1.25 equiv) in dichloromethane (100 mL). The reaction mixture was stirred at room temperature for 3 hours, diluted with dichloromethane (50 mL), and washed with water. The organic layer was dried over sodium sulfate, filtered, and concentrated under reduced pressure to yield 50 (6.7 g, 97% yield) as a colorless liquid which was used as such.

(6E,10E)-3-Bromo-2,6,10-trimethyl-12-((tetrahydro-2H-pyran-2-yl)oxy)dodeca-6,10-dien-2-ol (51)—N-Bromosuccinimide (4.28 g, 24.0 mmol, 1.1 equiv) was added in portions (10 minutes) to a solution of 50 (6.7 g, 21.9 mmol, 1 equiv) at 0° C. The reaction mixture was stirred at 0° C. for 2 hours. The mixture was diluted with diethyl ether (100 mL) and the layers were separated. The aqueous layer was extracted with diethyl ether (2×100 mL). The combined organic layer was dried over sodium sulfate, filtered, and concentrated under reduced pressure to yield 51 (9.0 g, quantitative yield) which was carried forward as such.

2-(((2E,6E)-9-(3,3-Dimethyloxiran-2-yl)-3,7-dimethyl-nona-2,6-dien-1-yl)oxy)tetrahydro-2H-pyran (52)—To a solution of 51 (9.0 g, 21.9 mmol, 1 equiv) in THF (120 mL) at 0° C. was added sodium hydride (1.3 g of a 60% dispersion in mineral oil, 33.5 mmol, 1.5 equiv). The reaction mixture was stirred for 1 hour at 0° C. followed by the addition of more sodium hydride (0.4 g, 11.1 mmol, 0.5 equiv). The reaction was continued for 3 hours and then quenched with saturated aqueous ammonium chloride (100 mL) and water (100 mL). The mixture was extracted with ethyl acetate (3×100 mL). The combined organic layer was washed with brine, dried over sodium sulfate, filtered, and concentrated under reduced pressure. The crude product was purified using an Analogix automated chromatography system eluting with a gradient of 10-25% ethyl acetate in heptanes yielding 52 (3.97 g, 55% yield) as a yellow oil.

(4E,8E)-4,8-Dimethyl-10-((tetrahydro-2H-pyran-2-yl)oxy)deca-4,8-dienal (53)—To a solution of 52 (3.97 g, 12.3 mmol, 1 equiv) in THF (60 mL) and water (60 mL) was added periodic acid (3.08 g, 13.5 mmol, 1.1 equiv). The reaction mixture was stirred at 0° C. for 2 hours and at room temperature for 2 hours. The reaction was diluted with water (100 mL) and extracted with ethyl acetate (1×100 mL). The organic layer was washed with brine (1×100 mL), dried over sodium sulfate, filtered, and concentrated under reduced pressure to yield 53 (3.0 g, 88% yield) as a colorless oil which was used as such.

Triphenyl(propan-2-yl-d7)phosphonium iodide (54)—A 40-mL vial was charged with 2-iodopropane-d7 (2.0 g, 11.3 mmol, 1 equiv, Cambridge Isotopes, 99.3 atom % D), toluene (10 mL), and triphenylphosphine (3.0 g, 11.3 mmol, 1 equiv). The vial was sealed and heated at 105° C. (external) for 1 week. The reaction was repeated on the same scale. The combined crude reaction mixtures were filtered and the solids washed with toluene (25 mL) and MTBE (25 mL). The solids were dried on the filter cake yielding 54 (5.6 g, 56% yield) as a white solid.

2-(((2E,6E)-3,7-Dimethyl-11-(methyl-d3)dodeca-2,6,10-trien-1-yl-12,12,12-d3)oxy)tetrahydro-2H-pyran (55)—To a solution of 54 (1.0 g, 2.28 mol, 1.3 equiv) in THF (8 mL) at 0° C. was added n-BuLi (1.5 mL of a 2.5 M solution in hexanes, 3.75 mmol, 2 equiv) dropwise. The mixture was stirred for 1 hour at 0° C. at which time 53 (0.48 g, 1.79 mmol, 1 equiv) was added as a solution in THF (2 mL). The reaction was stirred at room temperature overnight. The resulting solids were removed by filtration (washing with heptanes). The filtrate was concentrated under reduced pressure. The crude product was purified using an Analogix automated chromatography system eluting with 25% ethyl acetate in heptanes to yield 55 (280 mg, 53% yield) as a light yellow oil.

(2E,6E)-3,7-dimethyl-11-(methyl-d3)dodeca-2,6,10-trien-12,12,12-d3-1-ol (56)—A solution of 55 (280 mg, 0.90 mmol, 1 equiv) in methanol (3 mL) was treated with p-toluenesulfonic acid (43 mg, 0.22 mmol, 0.25 equiv) at room temperature for 40 hours. The reaction mixture was diluted with water and extracted with ethyl acetate (3×50 mL). The combined organic layer was concentrated under reduced pressure and the crude product was purified using an Analogix automated chromatography system eluting with a gradient of 0-25% ethyl acetate in heptanes to yield 56 (66 mg, 33% yield) as a clear oil. Note: Unreacted starting material was also recovered. $^1$H-NMR (CDCl$_3$, 400 MHz): δ 1.60 (s, 3H), 1.70 (s, 3H), 1.95-2.18 (m, 8H), 4.15 (d, 2H), 5.05-5.15 (m, 2H), 5.42 (t, 1H); MS (ESI): 228.2 (m/z).

Intermediate 46 is synthesized using appropriately deuterated intermediate 56 according to the literature procedures in *Bioorganic and Medicinal Chemistry Letters*, 2011, p. 3693-3698; *Bioorganic and Medicinal Chemistry*, 2006, p. 5389-5396; and *European Journal of Organic Chemistry*, 2014, p. 7684-7691; all of which are incorporated by reference in their entirety.

Example 3. Synthesis of Compound 166

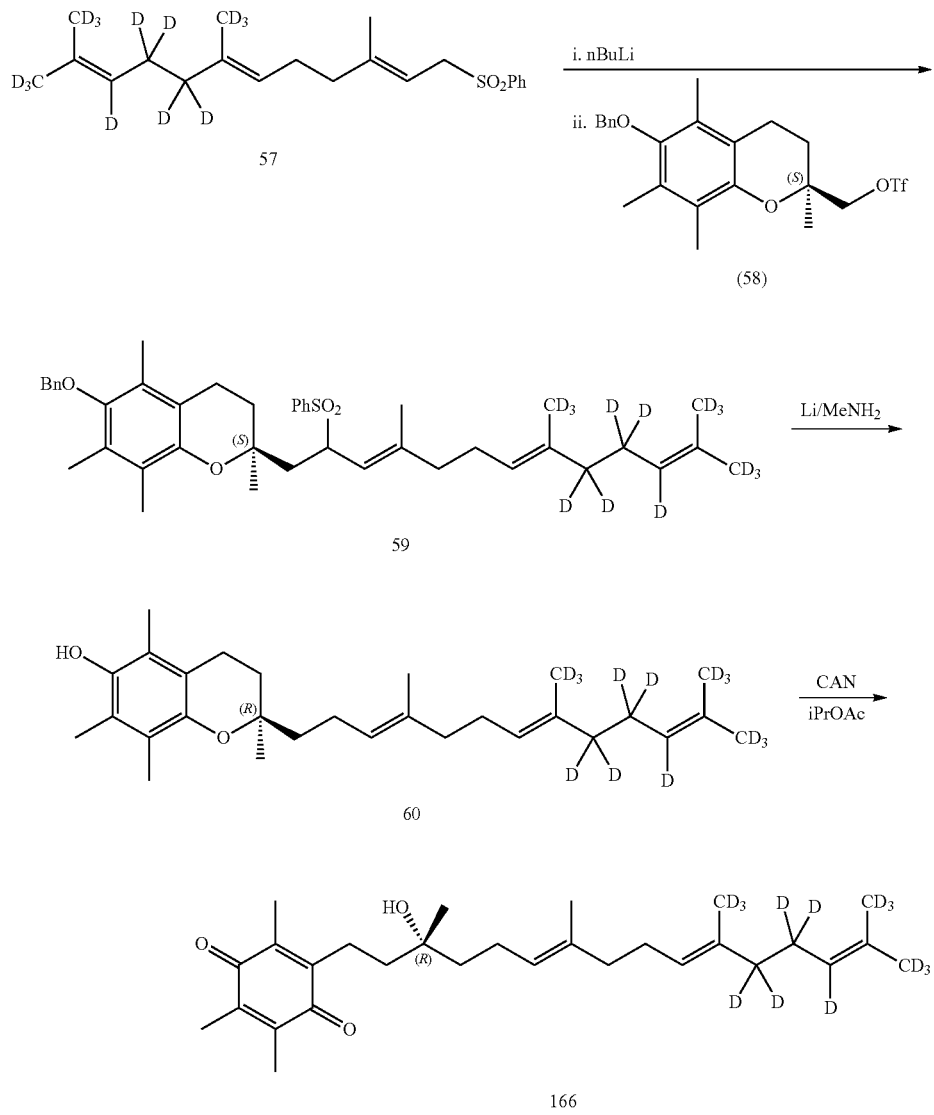

Compound 166 is synthesized from intermediates 57 and 58 according to the literature procedures in *Bioorganic and Medicinal Chemistry Letters*, 2011, p. 3693-3698; *Bioorganic and Medicinal Chemistry*, 2006, p. 5389-5396; and *European Journal of Organic Chemistry*, 2014, p. 7684-7691; all of which are incorporated by reference in their entirety.

Scheme 13: Preparation of Intermediate 57

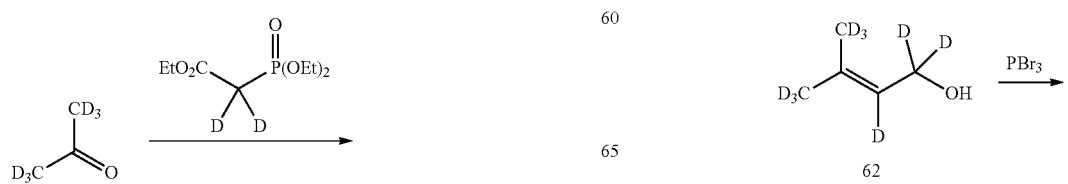

-continued

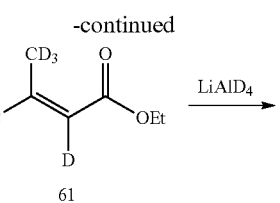

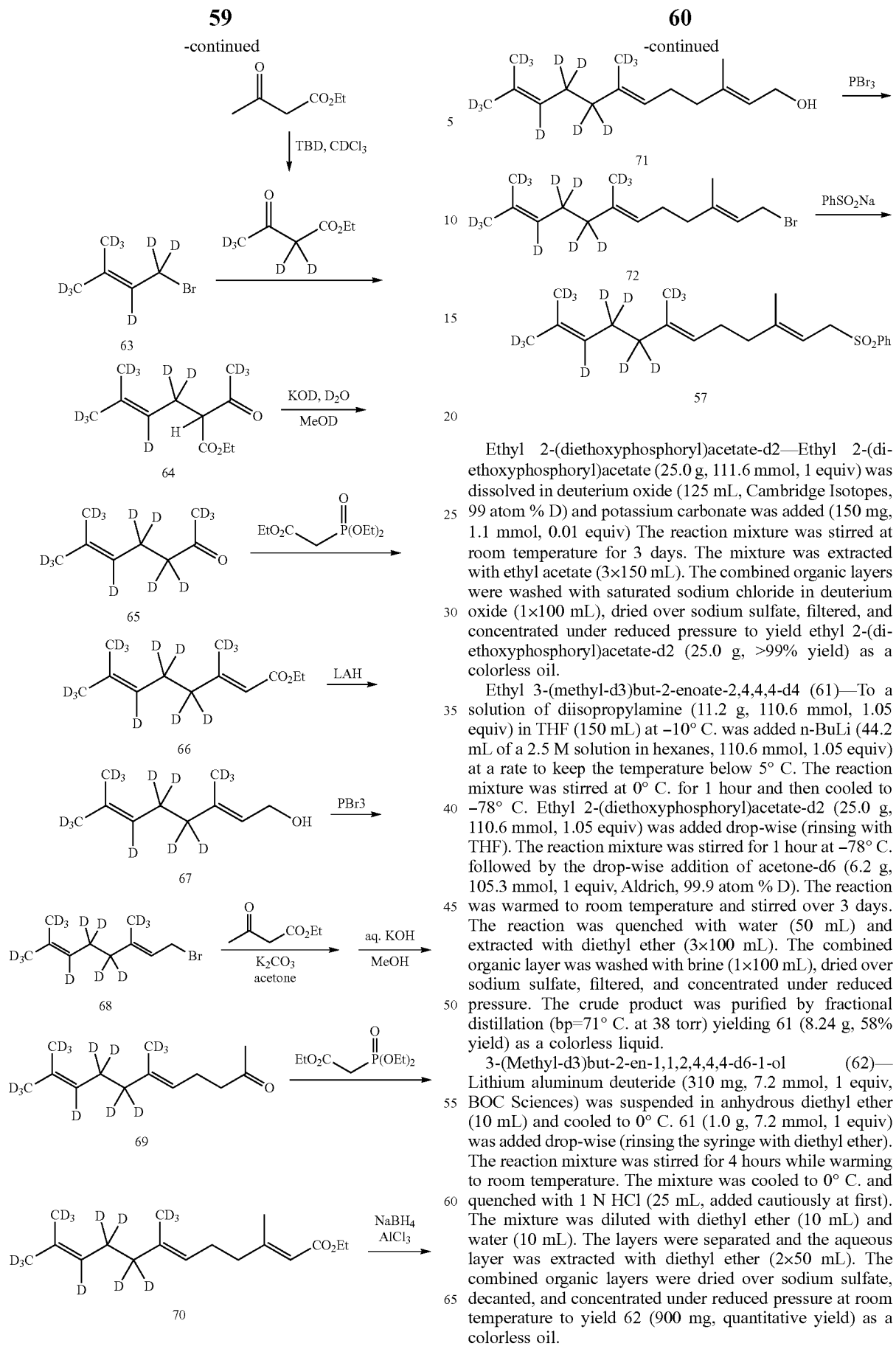

Ethyl 2-(diethoxyphosphoryl)acetate-d2—Ethyl 2-(diethoxyphosphoryl)acetate (25.0 g, 111.6 mmol, 1 equiv) was dissolved in deuterium oxide (125 mL, Cambridge Isotopes, 99 atom % D) and potassium carbonate was added (150 mg, 1.1 mmol, 0.01 equiv) The reaction mixture was stirred at room temperature for 3 days. The mixture was extracted with ethyl acetate (3×150 mL). The combined organic layers were washed with saturated sodium chloride in deuterium oxide (1×100 mL), dried over sodium sulfate, filtered, and concentrated under reduced pressure to yield ethyl 2-(diethoxyphosphoryl)acetate-d2 (25.0 g, >99% yield) as a colorless oil.

Ethyl 3-(methyl-d3)but-2-enoate-2,4,4,4-d4 (61)—To a solution of diisopropylamine (11.2 g, 110.6 mmol, 1.05 equiv) in THF (150 mL) at −10° C. was added n-BuLi (44.2 mL of a 2.5 M solution in hexanes, 110.6 mmol, 1.05 equiv) at a rate to keep the temperature below 5° C. The reaction mixture was stirred at 0° C. for 1 hour and then cooled to −78° C. Ethyl 2-(diethoxyphosphoryl)acetate-d2 (25.0 g, 110.6 mmol, 1.05 equiv) was added drop-wise (rinsing with THF). The reaction mixture was stirred for 1 hour at −78° C. followed by the drop-wise addition of acetone-d6 (6.2 g, 105.3 mmol, 1 equiv, Aldrich, 99.9 atom % D). The reaction was warmed to room temperature and stirred over 3 days. The reaction was quenched with water (50 mL) and extracted with diethyl ether (3×100 mL). The combined organic layer was washed with brine (1×100 mL), dried over sodium sulfate, filtered, and concentrated under reduced pressure. The crude product was purified by fractional distillation (bp=71° C. at 38 torr) yielding 61 (8.24 g, 58% yield) as a colorless liquid.

3-(Methyl-d3)but-2-en-1,1,2,4,4,4-d6-1-ol (62)—Lithium aluminum deuteride (310 mg, 7.2 mmol, 1 equiv, BOC Sciences) was suspended in anhydrous diethyl ether (10 mL) and cooled to 0° C. 61 (1.0 g, 7.2 mmol, 1 equiv) was added drop-wise (rinsing the syringe with diethyl ether). The reaction mixture was stirred for 4 hours while warming to room temperature. The mixture was cooled to 0° C. and quenched with 1 N HCl (25 mL, added cautiously at first). The mixture was diluted with diethyl ether (10 mL) and water (10 mL). The layers were separated and the aqueous layer was extracted with diethyl ether (2×50 mL). The combined organic layers were dried over sodium sulfate, decanted, and concentrated under reduced pressure at room temperature to yield 62 (900 mg, quantitative yield) as a colorless oil.

Intermediate 57 is synthesized from intermediate 62 according to the literature procedures in *Bioorganic and Medicinal Chemistry Letters,* 2011, p. 3693-3698; *Bioorganic and Medicinal Chemistry,* 2006, p. 5389-5396; and *European Journal of Organic Chemistry,* 2014, p. 7684-7691; all of which are incorporated by reference in their entirety.

washed with dichloromethane. The filtrate was concentrated under reduced pressure yielding 74 (2.7 g, 39% yield) as a white solid.

2-(Hydroxymethyl)-2,5,7,8-tetramethylchroman-6-ol (75)—A solution of lithium aluminum hydride (11.2 mL of a 1 M solution in THF, 11.2 mmol, 1.1 equiv) was added drop-wise to a cold (0° C.) solution of 74 (2.7 g, 10.2 mmol,

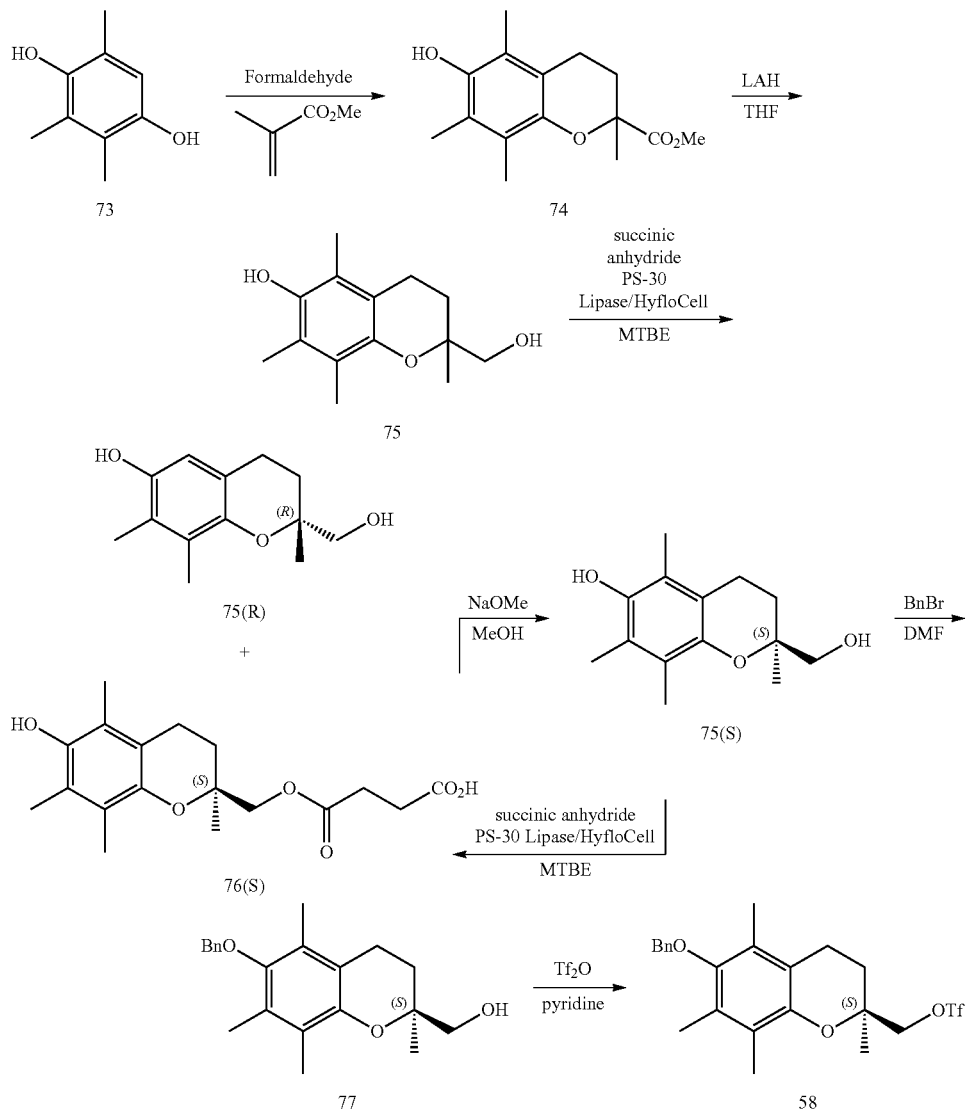

Methyl 6-hydroxy-2,5,7,8-tetramethylchromane-2-carboxylate (74)—A 35-mL microwave vial was charged with 73 (2.2 g, 13.2 mmol, 1 equiv), formaldehyde (2.2 g of a 37% solution in water with 10-15% methanol), and methyl methacrylate (6.6 g, 6.6 mmol, 5 equiv). The vial was sealed and heated at 160° C. for 3 hours. The reaction was repeated a second time at the same scale. Methanol (10 mL) was added to each crude reaction mixture and they were combined and stirred for 10 minutes. The solids were collected by vacuum filtration and washed with methanol. The solid was triturated with dichloromethane (50 mL), filtered, and 1 equiv) in THF (50 mL). The reaction mixture was warmed to room temperature and stirred for 4 hours resulting in a thick suspension. LC/MS analysis indicated incomplete conversion to product so additional lithium aluminum hydride (5.1 mL of a 1 M solution in THF, 5.1 mmol, 0.5 equiv) was added and the reaction mixture was stirred at room temperature overnight. The reaction mixture was cooled to 0° C. and quenched by the drop-wise addition of 1 N aqueous HCl (50 mL). The mixture was stirred for 30 minutes and then extracted with ethyl acetate (3×100 mL). The combined organic layer was washed with saturate brine (1×100 mL), dried over sodium sulfate, filtered, and concentrated under reduced pressure. The crude product was purified using an Analogix automated chromatography system eluting with a gradient of 0-2% methanol in dichloromethane to yield 75 (2.18 g, 92% yield) as a colorless oil which solidified upon standing.

(S)-4-((6-hydroxy-2,5,7,8-tetramethylchroman-2-yl) methoxy)-4-oxobutanoic acid (76(S) first cycle)—PS Amano Lipase (3.0 g, Aldrich #534641, Lot #MKBV0029V), Hyflosupercell (10 g), and 0.1 M $KH_2PO_4$ buffer pH=7 (10 mL) were shaken together for 10 minutes and then dried in a vacuum oven for 24 hours at 30° C. This solid supported lipase (4 g) was added to a solution of 75 (6.1 g, 25.8 mmol, 1 equiv) and succinic anhydride (3.62 g, 36.2 mmol, 1.4 equiv) in MTBE (150 mL). The mixture was stirred at room temperature overnight. The solids were removed by filtration through a pad of Celite (washing with MTBE). The filtrate was extracted with 10% aqueous sodium carbonate (3×100 mL). The organic layer (containing 75(R)) was set aside. The combined aqueous layer was treated with 1 N HCl to pH=3-4 and then extracted with dichloromethane (3×150 mL). The combined organic layer was dried over sodium sulfate, filtered, and concentrated under reduced pressure yielding 76(S) (5.3 g) as an orange oil which solidified on standing.

(S)-2-(Hydroxymethyl)-2,5,7,8-tetramethylchroman-6-ol (75(S))—76(S) (5.3 g, 15.8 mmol, 1 equiv, from above) was dissolved in methanol (60 mL) and the solution was sparged with a stream of nitrogen for 30 minutes. The solution was cooled to 0° C. and sodium methoxide (10 mL of a 25 wt % solution in methanol, 47.3 mmol, 3 equiv) was added. The reaction was warmed to room temperature and stirred for 3 hours. Water (100 mL) was added and the mixture was partially concentrated under reduced pressure. Saturated aqueous ammonium chloride was added to pH=8 and the aqueous mixture was extracted with MTBE (3×100 mL). The combined organic layer was washed with brine (1×150 mL), dried over sodium sulfate, filtered, and concentrated under reduced pressure to yield 75(S) (2.9 g) as a yellow oil. To ensure high enantiomeric purity, the above two steps were repeated yielding 75(S) (1.8 g, 59% yield after 2 cycles) as an off white solid in 98.2% ee (Chiracel OJ 25×4.6 mm, 80% heptane/20% 2-propanol at 0.3 mL/min Rt=24.9 min).

(S)-(6-(Benzyloxy)-2,5,7,8-tetramethylchroman-2-yl) methanol (77)—Benzyl bromide (1.33 mL, 11.3 mmol, 1.5 equiv) was added to a solution of 75(S) (1.76 g, 7.5 mmol, 1 equiv) and potassium carbonate (1.56 g, 11.3 mmol, 1.5 equiv) in DMF (15 mL). The reaction mixture was stirred at room temperature for 3 days at which time LC/MS analysis indicated 50% conversion to product. The reaction was quenched with water (100 mL) and extracted with MTBE (3×100 mL). The combined organic layer was washed with brine (1×100 mL), dried over sodium sulfate, filtered, and concentrated under reduced pressure yielding 2.6 g of crude product. The crude product was re-subjected to the above reaction conditions for an additional 24 hours resulting in >90% conversion. After repeating the above workup, the crude product was purified using an Analogix automated chromatography system eluting with a gradient of 10 to 50% ethyl acetate in heptanes yielding 77 (1.54 g, 63% yield) as a colorless oil.

(S)-(6-(Benzyloxy)-2,5,7,8-tetramethylchroman-2-yl) methyl trifluoromethanesulfonate (58)—A solution of 77 (326 mg, 1 mmol, 1 equiv) in pyridine (2 mL) was cooled to 0° C. and trifluoromethansulfonic anhydride (0.17 mL, 1 mmol, 1 equiv) was added. The reaction was stirred at 0° C. for 2 hours. Additional trifluoromethansulfonic anhydride was added (0.17 mL, 1 mmol, 1 equiv) and the reaction was stirred for an additional 1 hour at 0° C. The reaction was quenched with 1 N HCl (10 mL) and extracted with ethyl acetate (3×50 mL). The combined organic layer was washed with brine (1×50 mL), dried over sodium sulfate, filtered, and concentrated under reduced pressure. The crude product was purified using an Interchim automated chromatography system eluting with 0 to 40% ethyl acetate in heptanes to yield 58 (280 mg, 61% yield) as a white solid.

Example 4. Synthesis of Compound 169

Scheme 15: Preparation of Compound 169

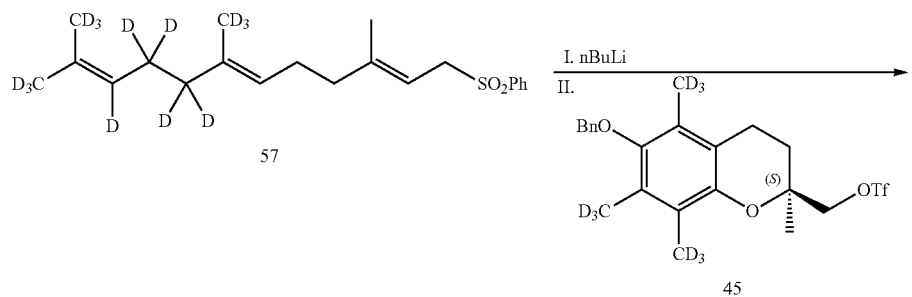

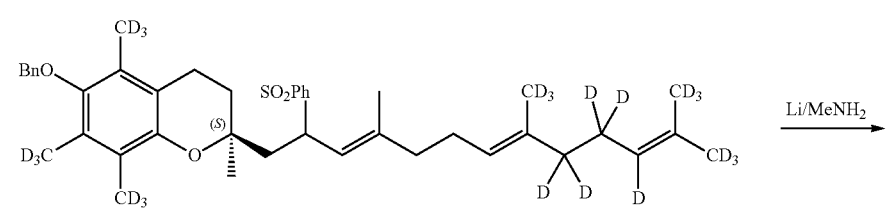

-continued

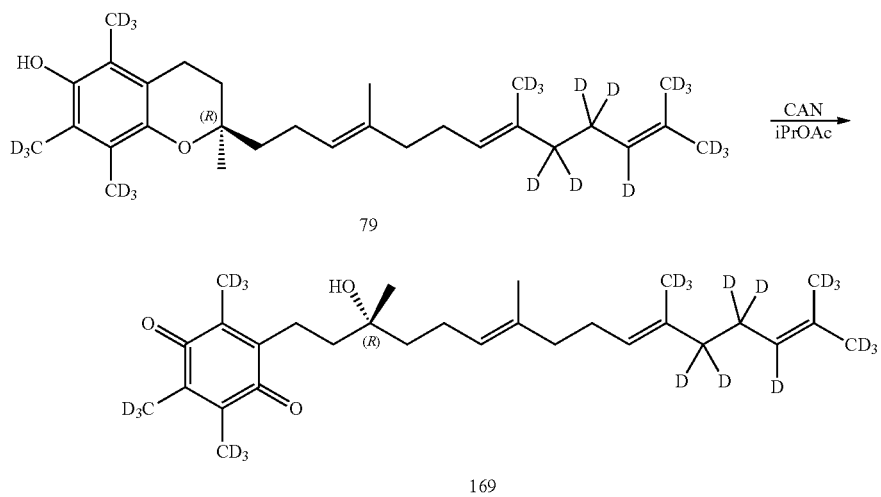

79

169

Compound 169 is synthesized as shown in Scheme 15 from intermediates 45 and 57 according to the literature procedures in *Bioorganic and Medicinal Chemistry Letters*, 2011, p. 3693-3698; *Bioorganic and Medicinal Chemistry*, 2006, p. 5389-5396; and *European Journal of Organic Chemistry*, 2014, p. 7684-7691; all of which are incorporated by reference in their entirety.

Example 5. Evaluation of Metabolic Stability

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I, Ia, II or IIa and the positive control, 7-ethoxycoumarin (1 µM). Testing is done in triplicate.

Data analysis: The in vitro $t_{1/2}$s for test compounds are calculated from the slopes of the linear regression of % parent remaining (ln) vs incubation time relationship.

in vitro $t_{1/2} = 0.693/k$ $k = -$[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A compound of Formula Ia:

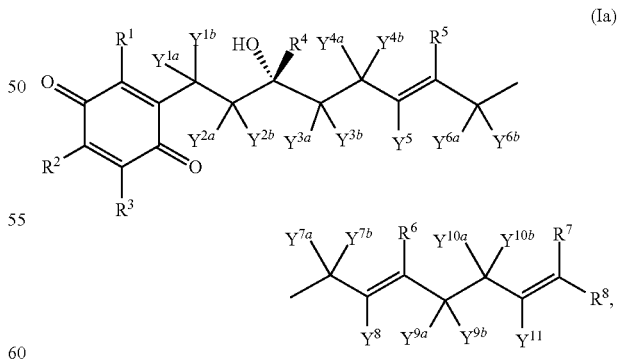

(Ia)

or a pharmaceutically acceptable salt thereof, wherein:
each of $R^1$, $R^2$, $R^3$, $R^4$, $R^5$, and $R^6$ is independently selected from —$CH_3$ and —$CD_3$;
each of $R^7$ and $R^8$ is —$CD_3$;
$Y^{1a}$ and $Y^{1b}$ are the same and are each hydrogen or each deuterium;

$Y^{2a}$ and $Y^{2b}$ are the same and are each hydrogen or each deuterium;
$Y^{3a}$ and $Y^{3b}$ are the same and are each hydrogen or each deuterium;
$Y^{4a}$ and $Y^{4b}$ are the same and are each hydrogen or each deuterium;
$Y^{6a}$ and $Y^{6b}$ are the same and are each hydrogen or each deuterium;
$Y^{7a}$ and $Y^{7b}$ are the same and are each hydrogen or each deuterium;
$Y^{9a}$ and $Y^{9b}$ are the same and are each hydrogen or each deuterium;
$Y^{10a}$ and $Y^{10b}$ are the same and are each deuterium;
each of $Y^5$ and $Y^8$ is independently selected from hydrogen and deuterium; and
$Y^{11}$ is deuterium.

2. The compound of claim 1, wherein $R^1$, $R^2$ and $R^3$ are the same.

3. The compound of claim 1, wherein at least one of $R^5$ and $R^6$ is —$CD_3$.

4. The compound of claim 1, wherein each of $Y^{9a}$, $Y^{9b}$ $Y^{10a}$, $Y^{10b}$, and $Y^{11}$ is the same.

5. The compound of claim 1, wherein each of $Y^{6a}$, $Y^{6b}$ $Y^{7a}$, $Y^{7b}$, and $Y^8$ is the same.

6. The compound of claim 1, wherein each of $Y^{3a}$, $Y^{3b}$ $Y^{4a}$, $Y^{4b}$, and $Y^5$ is the same.

7. The compound of claim 1, wherein each of $Y^{1a}$, $Y^{1b}$ $Y^{2a}$, and $Y^{2b}$ is the same.

8. The compound of claim 1, wherein any atom not designated as deuterium is present at its natural isotopic abundance.

9. The compound of claim 1, wherein the compound is selected from any one of:

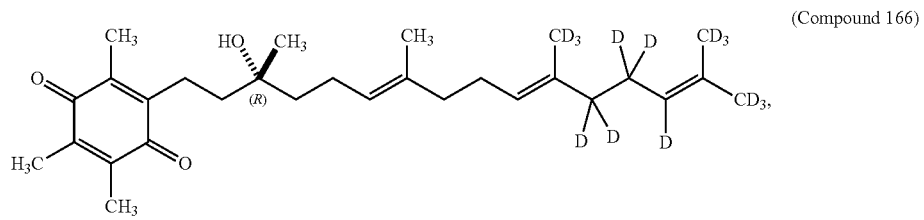

(Compound 166)

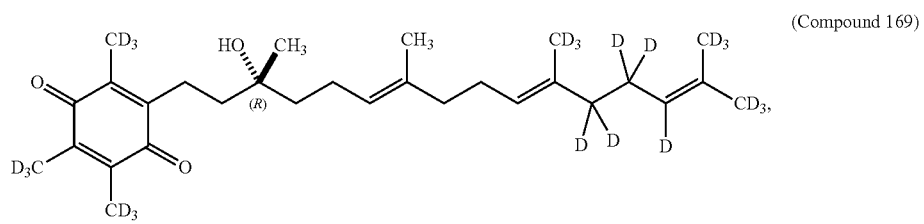

(Compound 169)

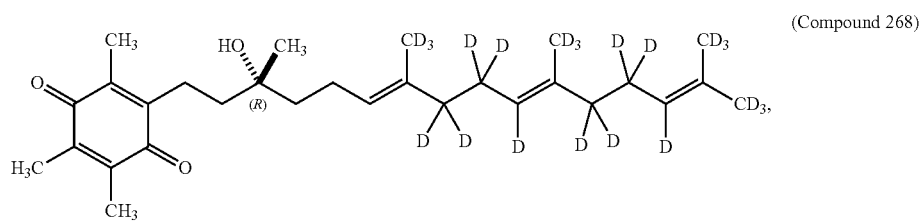

(Compound 268)

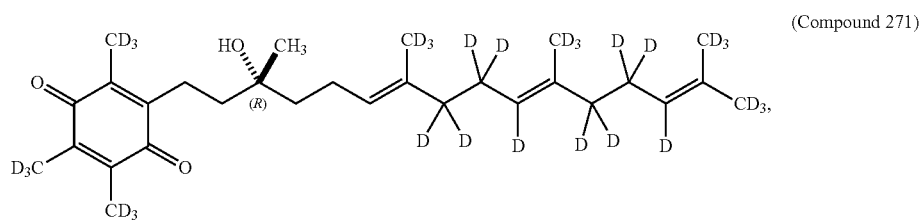

(Compound 271)

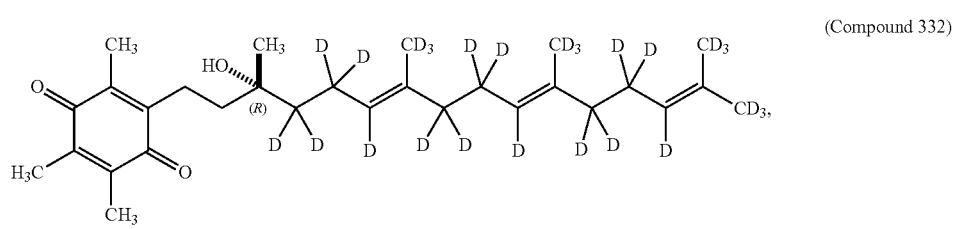

(Compound 332)

-continued

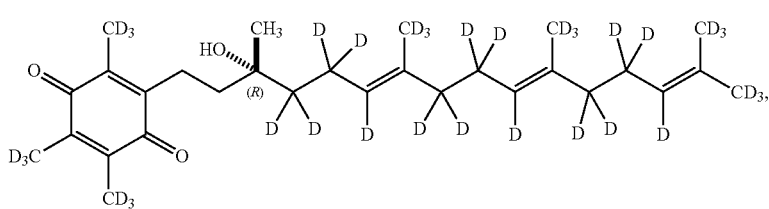
(Compound 335)

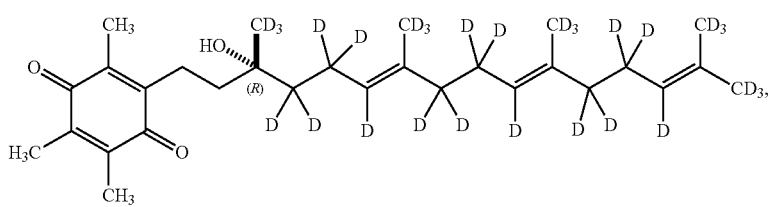
(Compound 336)

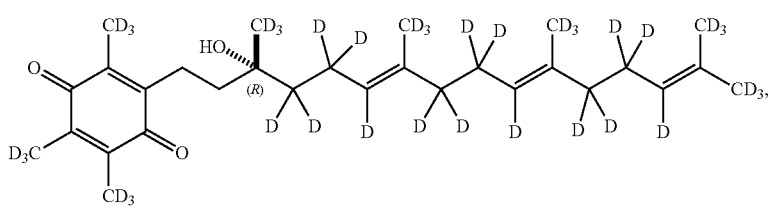
(Compound 337)

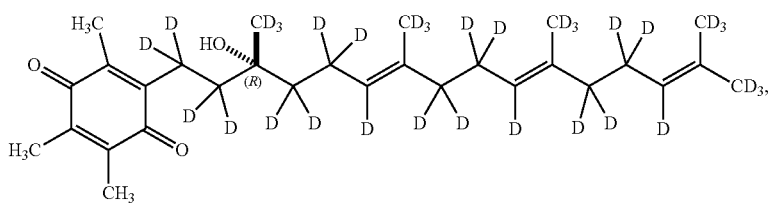
(Compound 352)

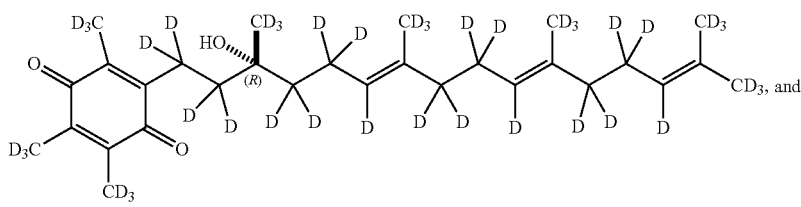
(Compound 353)

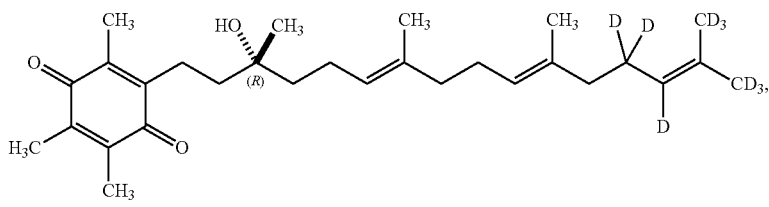
(Compound 357)

or a pharmaceutically acceptable salt thereof, and wherein any atom not designated as deuterium is present at its natural isotopic abundance.

10. The compound of claim 1, wherein the isotopic enrichment for each designated deuterium atom is at least 90%.

11. The compound of claim 10 wherein the isotopic enrichment for each designated deuterium atom is at least 95%.

12. The compound of claim 11 wherein the isotopic enrichment for each designated deuterium atom is at least 97%.

13. A pharmaceutical composition comprising a compound of claim 1; and a pharmaceutically acceptable carrier.

14. A method of treating a disease or condition selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, multisystem genetic disorders, Tourette's disease, metabolic disorders, mitochondrial disorders, Leber's hereditary optic neuropathy, and Huntington's disease in a subject comprising the step of administering to the subject in need thereof a compound of claim 1, or a pharmaceutically acceptable salt thereof.

15. The method of claim 14, wherein the disease or condition is selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, multisystem genetic disorders, Tourette's disease, and Leber's hereditary optic neuropathy.

16. The method of claim 15, wherein the disease or condition is Leigh syndrome.

17. A method of treating a disease or condition selected from Leigh syndrome, Friedreich's ataxia, Parkinson's disease, Pearson syndrome, cobalamin C deficiency syndrome, hearing loss, Rett's syndrome, autism spectrum disorders, inherited mitochondrial respiratory chain diseases, multisystem genetic disorders, Tourette's disease, metabolic disorders, mitochondrial disorders, Leber's hereditary optic neuropathy, and Huntington's disease in a subject comprising the step of administering to the subject in need thereof a pharmaceutical composition of claim 13.

18. The compound of claim 1, wherein $R^1$, $R^2$ and $R^3$ are the same; each of $Y^{1a}$, $Y^{1b}$ $Y^{2a}$, and $Y^{2b}$ is the same; each of $Y^{3a}$, $Y^{3b}$ $Y^{4a}$, $Y^{4b}$ and $Y^5$ is the same; each of $Y^{6a}$, $Y^{6b}$ $Y^{7a}$, $Y^{7b}$, and $Y^8$ is the same; each of $Y^{9a}$, $Y^{9b}$ $Y^{10a}$, $Y^{10b}$, and $Y^{11}$ is the same; and any atom not designated as deuterium is present at its natural isotopic abundance, wherein the compound is selected from any one of the compounds set forth in the following table:

| Compound # | $R^1/R^3/R^3$ | $R^4$ | $R^5$ | $R^6$ | $Y^{1a}/Y^{1b}/Y^{2a}/Y^{2b}$ | $Y^{3a}/Y^{3b}/Y^{4a}/Y^{4b}/Y^5$ | $Y^{6a}/Y^{6b}/Y^{7a}/Y^{7b}/Y^8$ | $Y^{9a}/Y^{9b}/Y^{10a}/Y^{10b}/Y^{11}$ |
|---|---|---|---|---|---|---|---|---|
| 163 | $CD_3$ | $CH_3$ | $CH_3$ | $CH_3$ | H | H | H | D |
| 164 | $CH_3$ | $CD_3$ | $CH_3$ | $CH_3$ | H | H | H | D |
| 165 | $CH_3$ | $CH_3$ | $CD_3$ | $CH_3$ | H | H | H | D |
| 166 | $CH_3$ | $CH_3$ | $CH_3$ | $CD_3$ | H | H | H | D |
| 167 | $CD_3$ | $CD_3$ | $CH_3$ | $CH_3$ | H | H | H | D |
| 168 | $CD_3$ | $CH_3$ | $CD_3$ | $CH_3$ | H | H | H | D |
| 169 | $CD_3$ | $CH_3$ | $CH_3$ | $CD_3$ | H | H | H | D |
| 170 | $CH_3$ | $CD_3$ | $CD_3$ | $CH_3$ | H | H | H | D |
| 171 | $CH_3$ | $CD_3$ | $CH_3$ | $CD_3$ | H | H | H | D |
| 172 | $CH_3$ | $CH_3$ | $CD_3$ | $CD_3$ | H | H | H | D |
| 173 | $CD_3$ | $CD_3$ | $CD_3$ | $CH_3$ | H | H | H | D |
| 174 | $CD_3$ | $CD_3$ | $CH_3$ | $CD_3$ | H | H | H | D |
| 175 | $CD_3$ | $CH_3$ | $CD_3$ | $CD_3$ | H | H | H | D |
| 176 | $CH_3$ | $CD_3$ | $CD_3$ | $CD_3$ | H | H | H | D |
| 177 | $CD_3$ | $CD_3$ | $CD_3$ | $CD_3$ | H | H | H | D |
| 178 | $CH_3$ | $CH_3$ | $CH_3$ | $CH_3$ | H | H | H | D |
| 211 | $CD_3$ | $CH_3$ | $CH_3$ | $CH_3$ | D | H | H | D |
| 212 | $CH_3$ | $CD_3$ | $CH_3$ | $CH_3$ | D | H | H | D |
| 213 | $CH_3$ | $CH_3$ | $CD_3$ | $CH_3$ | D | H | H | D |
| 214 | $CH_3$ | $CH_3$ | $CH_3$ | $CD_3$ | D | H | H | D |
| 215 | $CD_3$ | $CD_3$ | $CH_3$ | $CH_3$ | D | H | H | D |
| 216 | $CD_3$ | $CH_3$ | $CD_3$ | $CH_3$ | D | H | H | D |
| 217 | $CD_3$ | $CH_3$ | $CH_3$ | $CD_3$ | D | H | H | D |
| 218 | $CH_3$ | $CD_3$ | $CD_3$ | $CH_3$ | D | H | H | D |
| 219 | $CH_3$ | $CD_3$ | $CH_3$ | $CD_3$ | D | H | H | D |
| 220 | $CH_3$ | $CH_3$ | $CD_3$ | $CD_3$ | D | H | H | D |
| 221 | $CD_3$ | $CD_3$ | $CD_3$ | $CH_3$ | D | H | H | D |
| 222 | $CD_3$ | $CD_3$ | $CH_3$ | $CD_3$ | D | H | H | D |
| 223 | $CD_3$ | $CH_3$ | $CD_3$ | $CD_3$ | D | H | H | D |
| 224 | $CH_3$ | $CD_3$ | $CD_3$ | $CD_3$ | D | H | H | D |
| 225 | $CD_3$ | $CD_3$ | $CD_3$ | $CD_3$ | D | H | H | D |
| 226 | $CH_3$ | $CH_3$ | $CH_3$ | $CH_3$ | D | H | H | D |
| 243 | $CD_3$ | $CH_3$ | $CH_3$ | $CH_3$ | H | D | H | D |
| 244 | $CH_3$ | $CD_3$ | $CH_3$ | $CH_3$ | H | D | H | D |
| 245 | $CH_3$ | $CH_3$ | $CD_3$ | $CH_3$ | H | D | H | D |
| 246 | $CH_3$ | $CH_3$ | $CH_3$ | $CD_3$ | H | D | H | D |
| 247 | $CD_3$ | $CD_3$ | $CH_3$ | $CH_3$ | H | D | H | D |
| 248 | $CD_3$ | $CH_3$ | $CD_3$ | $CH_3$ | H | D | H | D |
| 249 | $CD_3$ | $CH_3$ | $CH_3$ | $CD_3$ | H | D | H | D |
| 250 | $CH_3$ | $CD_3$ | $CD_3$ | $CH_3$ | H | D | H | D |
| 251 | $CH_3$ | $CD_3$ | $CH_3$ | $CD_3$ | H | D | H | D |
| 252 | $CH_3$ | $CH_3$ | $CD_3$ | $CD_3$ | H | D | H | D |
| 253 | $CD_3$ | $CD_3$ | $CD_3$ | $CH_3$ | H | D | H | D |
| 254 | $CD_3$ | $CD_3$ | $CH_3$ | $CD_3$ | H | D | H | D |
| 255 | $CD_3$ | $CH_3$ | $CD_3$ | $CD_3$ | H | D | H | D |
| 256 | $CH_3$ | $CD_3$ | $CD_3$ | $CD_3$ | H | D | H | D |
| 257 | $CD_3$ | $CD_3$ | $CD_3$ | $CD_3$ | H | D | H | D |
| 258 | $CH_3$ | $CH_3$ | $CH_3$ | $CH_3$ | H | D | H | D |
| 259 | $CD_3$ | $CH_3$ | $CH_3$ | $CH_3$ | H | H | D | D |
| 260 | $CH_3$ | $CD_3$ | $CH_3$ | $CH_3$ | H | H | D | D |
| 261 | $CH_3$ | $CH_3$ | $CD_3$ | $CH_3$ | H | H | D | D |
| 262 | $CH_3$ | $CH_3$ | $CH_3$ | $CD_3$ | H | H | D | D |
| 263 | $CD_3$ | $CD_3$ | $CH_3$ | $CH_3$ | H | H | D | D |
| 264 | $CD_3$ | $CH_3$ | $CD_3$ | $CH_3$ | H | H | D | D |
| 265 | $CD_3$ | $CH_3$ | $CH_3$ | $CD_3$ | H | H | D | D |
| 266 | $CH_3$ | $CD_3$ | $CD_3$ | $CH_3$ | H | H | D | D |
| 267 | $CH_3$ | $CD_3$ | $CH_3$ | $CD_3$ | H | H | D | D |
| 268 | $CH_3$ | $CH_3$ | $CD_3$ | $CD_3$ | H | H | D | D |
| 269 | $CD_3$ | $CD_3$ | $CD_3$ | $CH_3$ | H | H | D | D |
| 270 | $CD_3$ | $CD_3$ | $CH_3$ | $CD_3$ | H | H | D | D |
| 271 | $CD_3$ | $CH_3$ | $CD_3$ | $CD_3$ | H | H | D | D |
| 272 | $CH_3$ | $CD_3$ | $CD_3$ | $CD_3$ | H | H | D | D |

-continued

| Compound # | R$^1$/R$^3$/R$^3$ | R$^4$ | R$^5$ | R$^6$ | Y$^{1a}$/Y$^{1b}$/Y$^{2a}$/Y$^{2b}$ | Y$^{3a}$/Y$^{3b}$/Y$^{4a}$/Y$^{4b}$/Y$^5$ | Y$^{6a}$/Y$^{6b}$/Y$^{7a}$/Y$^{7b}$/Y$^8$ | Y$^{9a}$/Y$^{9b}$/Y$^{10a}$/Y$^{10b}$/Y$^{11}$ |
|---|---|---|---|---|---|---|---|---|
| 273 | CD$_3$ | CD$_3$ | CD$_3$ | CD$_3$ | H | H | D | D |
| 274 | CH$_3$ | CH$_3$ | CH$_3$ | CH$_3$ | H | H | D | D |
| 291 | CD$_3$ | CH$_3$ | CH$_3$ | CH$_3$ | D | D | H | D |
| 292 | CH$_3$ | CD$_3$ | CH$_3$ | CH$_3$ | D | D | H | D |
| 293 | CH$_3$ | CH$_3$ | CD$_3$ | CH$_3$ | D | D | H | D |
| 294 | CH$_3$ | CH$_3$ | CH$_3$ | CD$_3$ | D | D | H | D |
| 295 | CD$_3$ | CD$_3$ | CH$_3$ | CH$_3$ | D | D | H | D |
| 296 | CD$_3$ | CH$_3$ | CD$_3$ | CH$_3$ | D | D | H | D |
| 297 | CD$_3$ | CH$_3$ | CH$_3$ | CD$_3$ | D | D | H | D |
| 298 | CH$_3$ | CD$_3$ | CD$_3$ | CH$_3$ | D | D | H | D |
| 299 | CH$_3$ | CD$_3$ | CH$_3$ | CD$_3$ | D | D | H | D |
| 300 | CH$_3$ | CH$_3$ | CD$_3$ | CD$_3$ | D | D | H | D |
| 301 | CD$_3$ | CD$_3$ | CD$_3$ | CH$_3$ | D | D | H | D |
| 302 | CD$_3$ | CD$_3$ | CH$_3$ | CD$_3$ | D | D | H | D |
| 303 | CD$_3$ | CH$_3$ | CD$_3$ | CD$_3$ | D | D | H | D |
| 304 | CH$_3$ | CD$_3$ | CD$_3$ | CD$_3$ | D | D | H | D |
| 305 | CD$_3$ | CD$_3$ | CD$_3$ | CD$_3$ | D | D | H | D |
| 306 | CH$_3$ | CH$_3$ | CH$_3$ | CH$_3$ | D | D | H | D |
| 307 | CD$_3$ | CH$_3$ | CH$_3$ | CH$_3$ | D | H | D | D |
| 308 | CH$_3$ | CD$_3$ | CH$_3$ | CH$_3$ | D | H | D | D |
| 309 | CH$_3$ | CH$_3$ | CD$_3$ | CH$_3$ | D | H | D | D |
| 310 | CH$_3$ | CH$_3$ | CH$_3$ | CD$_3$ | D | H | D | D |
| 311 | CD$_3$ | CD$_3$ | CH$_3$ | CH$_3$ | D | H | D | D |
| 312 | CD$_3$ | CH$_3$ | CD$_3$ | CH$_3$ | D | H | D | D |
| 313 | CD$_3$ | CH$_3$ | CH$_3$ | CD$_3$ | D | H | D | D |
| 314 | CH$_3$ | CD$_3$ | CD$_3$ | CH$_3$ | D | H | D | D |
| 315 | CH$_3$ | CD$_3$ | CH$_3$ | CD$_3$ | D | H | D | D |
| 316 | CH$_3$ | CH$_3$ | CD$_3$ | CD$_3$ | D | H | D | D |
| 317 | CD$_3$ | CD$_3$ | CD$_3$ | CH$_3$ | D | H | D | D |
| 318 | CD$_3$ | CD$_3$ | CH$_3$ | CD$_3$ | D | H | D | D |
| 319 | CD$_3$ | CH$_3$ | CD$_3$ | CD$_3$ | D | H | D | D |
| 320 | CH$_3$ | CD$_3$ | CD$_3$ | CD$_3$ | D | H | D | D |
| 321 | CD$_3$ | CD$_3$ | CD$_3$ | CD$_3$ | D | H | D | D |
| 322 | CH$_3$ | CH$_3$ | CH$_3$ | CH$_3$ | D | H | D | D |
| 323 | CD$_3$ | CH$_3$ | CH$_3$ | CH$_3$ | H | D | D | D |
| 324 | CH$_3$ | CD$_3$ | CH$_3$ | CH$_3$ | H | D | D | D |
| 325 | CH$_3$ | CH$_3$ | CD$_3$ | CH$_3$ | H | D | D | D |
| 326 | CH$_3$ | CH$_3$ | CH$_3$ | CD$_3$ | H | D | D | D |
| 327 | CD$_3$ | CD$_3$ | CH$_3$ | CH$_3$ | H | D | D | D |
| 328 | CD$_3$ | CH$_3$ | CD$_3$ | CH$_3$ | H | D | D | D |
| 329 | CD$_3$ | CH$_3$ | CH$_3$ | CD$_3$ | H | D | D | D |
| 330 | CH$_3$ | CD$_3$ | CD$_3$ | CH$_3$ | H | D | D | D |
| 331 | CH$_3$ | CD$_3$ | CH$_3$ | CD$_3$ | H | D | D | D |
| 332 | CH$_3$ | CH$_3$ | CD$_3$ | CD$_3$ | H | D | D | D |
| 333 | CD$_3$ | CD$_3$ | CD$_3$ | CH$_3$ | H | D | D | D |
| 334 | CD$_3$ | CD$_3$ | CH$_3$ | CD$_3$ | H | D | D | D |
| 335 | CD$_3$ | CH$_3$ | CD$_3$ | CD$_3$ | H | D | D | D |
| 336 | CH$_3$ | CD$_3$ | CD$_3$ | CD$_3$ | H | D | D | D |
| 337 | CD$_3$ | CD$_3$ | CD$_3$ | CD$_3$ | H | D | D | D |
| 338 | CH$_3$ | CH$_3$ | CH$_3$ | CH$_3$ | H | D | D | D |
| 339 | CD$_3$ | CH$_3$ | CH$_3$ | CH$_3$ | D | D | D | D |
| 340 | CH$_3$ | CD$_3$ | CH$_3$ | CH$_3$ | D | D | D | D |
| 341 | CH$_3$ | CH$_3$ | CD$_3$ | CH$_3$ | D | D | D | D |
| 342 | CH$_3$ | CH$_3$ | CH$_3$ | CD$_3$ | D | D | D | D |
| 343 | CD$_3$ | CD$_3$ | CH$_3$ | CH$_3$ | D | D | D | D |
| 344 | CD$_3$ | CH$_3$ | CD$_3$ | CH$_3$ | D | D | D | D |
| 345 | CD$_3$ | CH$_3$ | CH$_3$ | CD$_3$ | D | D | D | D |
| 346 | CH$_3$ | CD$_3$ | CD$_3$ | CH$_3$ | D | D | D | D |
| 347 | CH$_3$ | CD$_3$ | CH$_3$ | CD$_3$ | D | D | D | D |
| 348 | CH$_3$ | CH$_3$ | CD$_3$ | CD$_3$ | D | D | D | D |
| 349 | CD$_3$ | CD$_3$ | CD$_3$ | CH$_3$ | D | D | D | D |
| 350 | CD$_3$ | CD$_3$ | CH$_3$ | CD$_3$ | D | D | D | D |
| 351 | CD$_3$ | CH$_3$ | CD$_3$ | CD$_3$ | D | D | D | D |
| 352 | CH$_3$ | CD$_3$ | CD$_3$ | CD$_3$ | D | D | D | D |
| 353 | CD$_3$ | CD$_3$ | CD$_3$ | CD$_3$ | D | D | D | D |
| 354 | CH$_3$ | CH$_3$ | CH$_3$ | CH$_3$ | D | D | D | D | or a pharmaceutically acceptable salt thereof, wherein the isotopic enrichment for each designated deuterium atom is at least 90%.

19. The compound of claim 1, wherein the compound is (Compound 357)

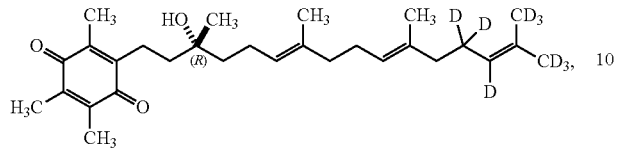

or a pharmaceutically acceptable salt thereof, wherein any atom not designated as deuterium is present at its natural isotopic abundance.

20. The compound of claim 18, wherein the isotopic enrichment for each designated deuterium atom is at least 90%.

21. The compound of claim 19, wherein the isotopic enrichment for each designated deuterium atom is at least 95%.

* * * * *